US011699527B2

(12) United States Patent
Krasik et al.

(10) Patent No.: US 11,699,527 B2
(45) Date of Patent: Jul. 11, 2023

(54) METHOD FOR IMPROVING DISEASE DIAGNOSIS USING MEASURED ANALYTES

(71) Applicant: OTRACES INC., Rockville, MD (US)

(72) Inventors: Galina Krasik, Rockville, MD (US); Mohsen Marefat, Rockville, MD (US); Keith Lingenfelter, Rockville, MD (US)

(73) Assignee: Otraces, Inc., Gaithersburg, MD (US)

( * ) Notice: Subject to any disclaimer, the term of this patent is extended or adjusted under 35 U.S.C. 154(b) by 838 days.

(21) Appl. No.: 14/774,491

(22) PCT Filed: Mar. 13, 2014

(86) PCT No.: PCT/US2014/000041
§ 371 (c)(1),
(2) Date: Sep. 10, 2015

(87) PCT Pub. No.: WO2014/158287
PCT Pub. Date: Oct. 2, 2014

(65) Prior Publication Data
US 2016/0034651 A1 Feb. 4, 2016

Related U.S. Application Data

(60) Provisional application No. 61/851,867, filed on Mar. 14, 2013.

(51) Int. Cl.
G01N 33/48 (2006.01)
G16H 50/20 (2018.01)
G06N 20/00 (2019.01)
G16B 20/00 (2019.01)
G16B 40/00 (2019.01)
G16H 50/30 (2018.01)

(52) U.S. Cl.
CPC ............ *G16H 50/20* (2018.01); *G06N 20/00* (2019.01); *G16B 20/00* (2019.02); *G16B 40/00* (2019.02); *G16H 50/30* (2018.01)

(58) Field of Classification Search
None
See application file for complete search history.

(56) References Cited

U.S. PATENT DOCUMENTS

| 6,058,322 | A | 5/2000 | Nishikawa et al. |
| 7,604,956 | B2 | 10/2009 | Drukier |
| 9,952,220 | B2 | 4/2018 | Michalek et al. |
| 2003/0032017 | A1* | 2/2003 | Anderson ........ G01N 27/44773 435/6.12 |
| 2004/0047493 | A1* | 3/2004 | Rowe ................ A61B 5/0059 382/115 |
| 2004/0121343 | A1 | 6/2004 | Buechler et al. |
| 2005/0272110 | A1* | 12/2005 | Drukier .............. G01N 33/60 435/7.93 |
| 2008/0133141 | A1 | 6/2008 | Frost |
| 2008/0286776 | A1 | 11/2008 | Young |
| 2009/0234627 | A1 | 9/2009 | Yu et al. |
| 2009/0263827 | A1 | 10/2009 | Johansen |
| 2011/0123976 | A1 | 5/2011 | Raftery |
| 2011/0178273 | A1* | 7/2011 | Aabersold .......... G01N 33/6848 530/350 |
| 2012/0022793 | A1 | 1/2012 | Baker et al. |
| 2012/0132540 | A1* | 5/2012 | Wang ................ A61B 5/14532 205/775 |
| 2012/0315641 | A1 | 12/2012 | Dubinett et al. |
| 2013/0261010 | A1* | 10/2013 | Bailey .................. G01N 27/72 506/9 |
| 2013/0316374 | A1 | 11/2013 | Penninger et al. |
| 2014/0194304 | A1* | 7/2014 | Shi ........................ G01N 33/50 506/9 |
| 2014/0274794 | A1* | 9/2014 | Speicher ............ C07K 14/4748 506/9 |
| 2016/0034651 | A1 | 2/2016 | Krasik et al. |
| 2017/0281725 | A1 | 10/2017 | Sims et al. |
| 2017/0372023 | A1 | 12/2017 | Krasik |

FOREIGN PATENT DOCUMENTS

| CN | 105005680 A | 10/2015 |
| CN | 105209631 | 12/2015 |
| JP | S60-209177 | 10/1985 |
| JP | 2011528442 A | 11/2011 |
| WO | WO-2010009337 A2 | 1/2010 |
| WO | WO-2012037603 A1 | 3/2012 |
| WO | PCT/JP2015/514208 | 6/2012 |
| WO | WO-2014-149629 | 9/2014 |
| WO | WO-2014/158287 A2 | 10/2014 |
| WO | WO 2016/115511 A2 | 7/2016 |
| WO | WO-2017/127822 A1 | 7/2017 |

OTHER PUBLICATIONS

Nagalla, Srinivasa R., et al. "Proteomic analysis of maternal serum in down syndrome: identification of novel protein biomarkers." Journal of proteome research 6.4 (2007): 1245-1257.*
Ahmed, Nuzhat, et al. "An approach to remove albumin for the proteomic analysis of low abundance biomarkers in human serum." Proteomics 3.10 (2003): 1980-1987.*
International Search Report/Written Opinion for PCT/US/2018/46056 dated Oct. 26, 2018.
Drukier et al., "High-Sensitivity Blood-Based Detection of Breast Cancer by Multi Photon Detection Diagnostic Proteomics"; Journal of Proteome Research, 5(8) Aug. 1, 2006, 1906-1915, XP55350821.
Evaluation of HE4, CA125, risk of ovarian malignancy algorithm (ROMA) and risk of malignancy index (RMI) as diagnostic tools of epithelial ovarian cancer in patients with a pelvic mass; Mona Aarenstrup Karlsen, Noreen Sandhu, Claus Høgdall, Ib Jarle Christensen, Lotte Nedergaard, Lene Lundvall, Svend A.Engelholm, Anette T.Pedersen, Dorthe Hartwell, Magnus Lydolph, Inga Alice Laursen, Estrid V.S.Høgdall; Gynecologic Oncology, vol. 127, Issue 2, Nov. 2012, pp. 379-383.

(Continued)

*Primary Examiner* — Anna Skibinsky
(74) *Attorney, Agent, or Firm* — Blank Rome LLP

(57) ABSTRACT

Methods for improving clinical diagnostic tests are provided, along with associated diagnostic techniques.

20 Claims, 13 Drawing Sheets

(56) References Cited

OTHER PUBLICATIONS

Performance of a Multiplexed Dual Analyte Immunoassay for the Early Detection of non-small cell lung cancer; Victoria Doseeva, Tracy Colpitts, Grace Gao, Juliana Woodstock and Vladimir Knezevic, Journal of Translational Medicine, (2015) 13:55, DOI 10.1186/s12967-015-0419-y.

Thesis "Network-Based Biomarker Discovery: Development of Prognostic Biomarkers for Personalized Medicine by Integrating Data and Prior Knowledge"; Dissertation zur Erlangung des Doktorgrades Jan. 1, 2014 (Jan. 1, 2014).

"Building Multidimensional Biomarker Views of Type 2 Diabetes on the Basis of Protein Microheterogeneity", Clinical Chemistry 57:5 719-728. Borges et al.; Jan. 1, 2011 (Jan. 1, 2011).

Song et al., "Identification of Serum Biomarkers for Lung Cancer Using Magnetic Bead-Based SELDI-TOF-MS," Acta Pharmacologica Sinica (2011) 32: 1537-1542.

Malik et al., "Soluble Adhesion Molecules and Prediction of Coronary Heart Disease: A Prospective Study and Meta-Analysis," The Lancet, Sep. 22, 2001, vol. 358; pp. 971-975.

International Preliminary Reporton Patentability in International Application No. PCT/US2014/000041, dated Sep. 15, 2015.

International Search Report in International Application No. PCT/US2014/000041, dated Sep. 25, 2014.

Lokshin et al., "Multimarker assay for early diagnosis of ovarian cancer," American Association for Cancer Research, *Amer Assoc Cancer Res* 2006, 47: 653, CME: Disclosure.

Drukier et al., "Ultra-Sensitive Immunoassays Using Multi Photon Detection in Diagnostic Proteomics of Blood," *Journal of Proteome Research* 2005, 4:2375-2378.

European Search Report in EP Appln. No. 147765382, dated Mar. 9, 2017.

Woelfel et al., "Orthogonal Rotation to Theoretical Criteria," pp. 1-20.

Torgerson, Warrenton, "Multidimensional Scaling: I. Theory and Method", *Psychometrika*, vol. 17, No. 4, Dec. 1952.

Toss, Angela et al. "Molecular Biomarkers for Prediction of Targeted Therapy Response in Metastatic Breast Cancer: Trick or Treat?." *International Journal of Molecular Sciences*, vol. 18, 1 85. Jan. 4, 2017, doi:10.3390/ijms18010085 (Year: 2017).

Office Action dated Mar. 29, 2023 issued in corresponding CN Application No. 201880065502.9.

\* cited by examiner

Figure 1 Training Set and Diagnostic Flow Chart
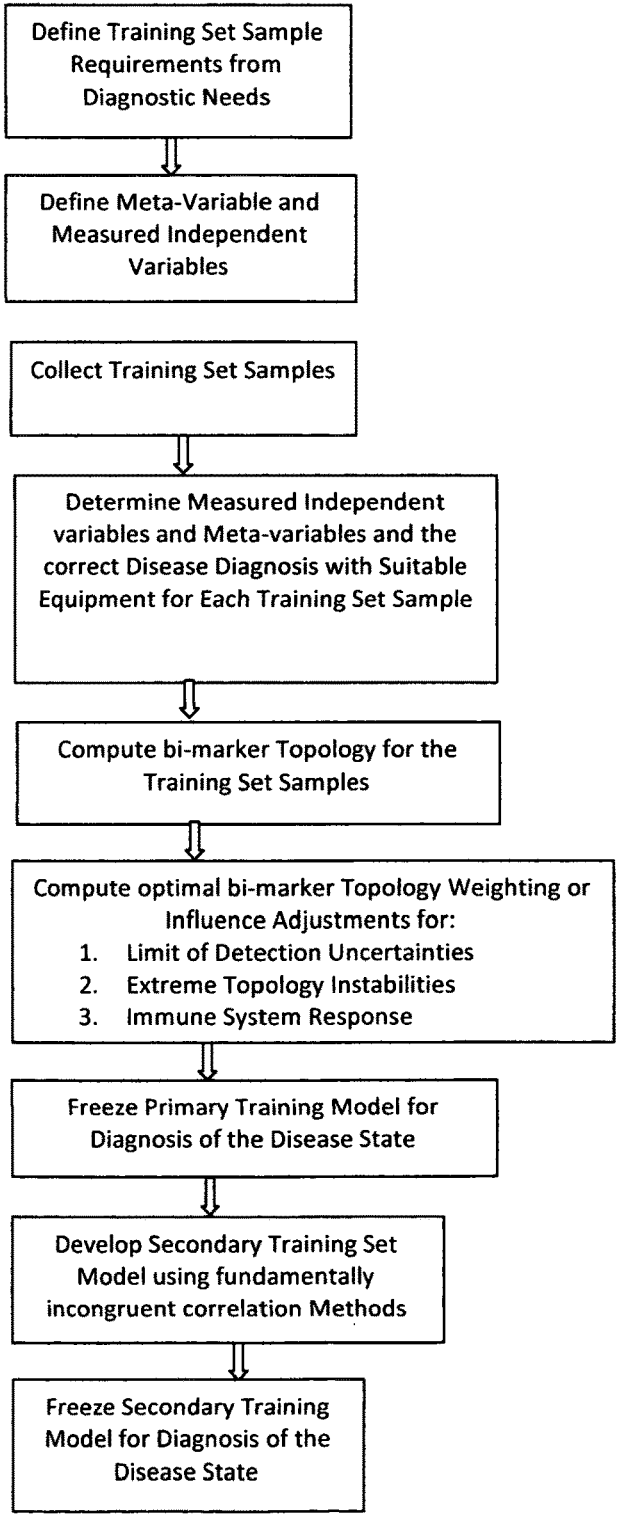
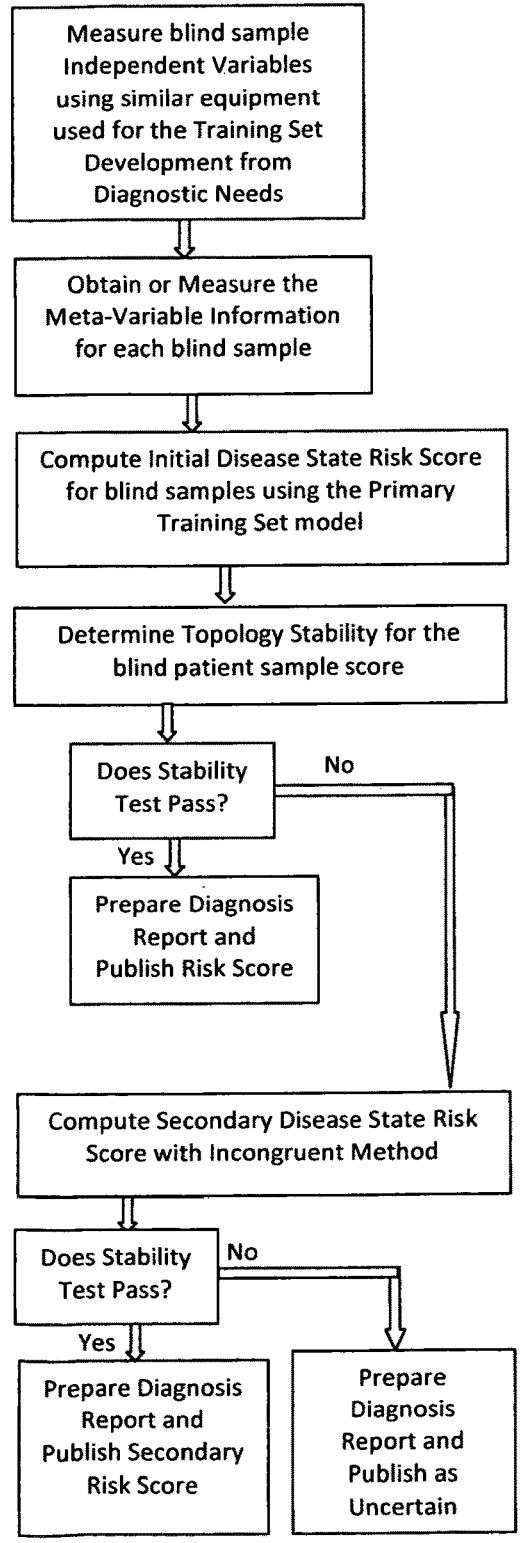

Error Range for 5% Cancer Score Error

METHOD FOR IMPROVING DISEASE DIAGNOSIS USING MEASURED ANALYTES

TECHNICAL FIELD

The present invention relates to methods for improving the accuracy of disease diagnosis and to associated diagnostic tests involving the correlation of measured analytes with binary outcomes.

BACKGROUND

Correlation methods where three or more independent variables are used to correlate a binary outcome (such as the presence or absence of a given disease) are commonly used with the cluster or neighborhood search method, the regression method and the wavelet methods. In the case of disease prediction, common constituents of blood or serum are measured and a correlation is attempted using these concentrations as independent variables for various disease state predictions. In the case of a given disease state where the outcome is either "disease" or "not disease," the logistic regression method is commonly used. Other techniques involve, for example, genetic algorithms. The predictive power of these methods is highly dependent on the constituent analytes chosen for the method. Persons skilled in the art recognize that many analytes and parameters that would seem to have predictive power do not improve diagnostic and analytical power in practice.

The regression method uses trends in the independent variables to correlate with the outcomes. The linear method is based on linear trends and logistic regression is based upon logarithmic trends. In biological disease prediction commonly logistic regression is used.

The group clustering method surveys a variable correlation topology for grouping of like outcomes. The clustering method has the advantage that it can find correlations where trends are not contiguous but have topology local reversals in trends. This method though highly non-linear and susceptible to local highly variable outcomes with small measurement errors can be more predictive in biological uses. Additionally, both methods can be combined with generally the cluster method applied small scale on an overall regression method.

However, some independent variables that would logically seem to have a correlation in practice do not show a predictive trend. Thus, what has been needed is an approach that improves diagnostic accuracy by utilizing patient-specific and population-specific variables that heretofore have not contributed useful information to the diagnosis of disease states.

Much research has been done to find biomarkers that alone or in combination can predict disease states with sufficient reproducibility and predictive power for clinical use. This research has had limited or no success. High Abundance Proteins (HAPs) have been heavily researched to find a single protein that can make this prediction. Numerous examples have been found but none have sufficiently low levels of false negatives to allow screening patients for the disease with the marker. As a result, such single biomarkers are used for only therapy monitoring with the exception of PSA for prostate cancer. This test requires that the concentration that indicates a biopsy would be appropriate be heavily skewed to lower false negatives resulting in very high levels of false positives. As much as 80% of the men who are indicated to need biopsy are actually negative for prostate cancer.

DNA markers also have been found to be very good in some cases for a sub-type of a cancer, but again are not suitable for screening for the same reasons as the HAPs noted above.

Using multiple proteins, proteomic approaches have also been investigated. This work has focused on, again, HAPs or on high level effecter proteins. This work has been dominated by multiplex methods of protein measurement such as immunoassays, chips and mass spectrophotometry. Very early work has found some success with ovarian cancer. However, a problem with all of these methods is that many of the proteins selected do not have a strong correlation with progression from healthy to disease (and many do not have a known biological connection with a disease state, for example, as typically is the case with mass spectrometry). Furthermore, mass spectrometry suffers a serious oversampling problem due to the fact that the whole serum sample is interrogated by the spectrophotometer for protein levels and thus the training of the correlation algorithm is difficult. In the mass spectrometry case, the whole serum sample may have over 200 proteins and 10,000 mass spec peaks.

What also has been needed in the diagnostic field are techniques that utilize lower abundance proteins that are more useful for diagnostic purposes than are HAPS, as well as analytical techniques that provide for analysis of low abundance biomarkers.

SUMMARY

The invention and various embodiments are set out in the claims that form part of this patent application. Without limiting the foregoing, in a preferred aspect, in a preferred embodiment, the invention relates to improving the predictive power and diagnostic accuracy of methods for predicting disease states using multi-variable (multi-variant) correlation methods. These methods include proteomic, metabolomic and other techniques that involve the determination of levels of various biomarkers as found in bodily fluids and tissue samples.

Various embodiments contemplated by the inventors and discussed in this application include the use of meta-variables, particularly using methods that adjust the influence of measured biomarker analytes on a correlation score. Such meta-variables may be identified based upon special knowledge of immune system response and knowledge of possible measurement errors. These methods can be applied to either the construction of the training set model or to the blind samples under diagnosis.

In one embodiment, the present invention relates to a method for diagnosing a disease, comprising the steps of: a) determining the concentrations of at least three predetermined analytes in a blind sample from a subject; b) selecting one or more meta-variable associated with the subject, which varies in a population associated with the subject for members of the population who are known either to have or not have the disease; c) transforming the concentrations of the analytes as a function of one or more population distribution characteristics and the one or more meta-variables to compute a pseudo-concentration that represents each analyte; d) comparing the pseudo-concentrations to a training set model of pseudo-concentrations determined for members of the population who are known either to have or not have the disease; and e) determining whether the comparison indicates that the subject has the disease. It is contemplated that the step (a) of determining the concentrations (or levels) of predetermined analytes may be performed in a separate time and place from the remaining steps of the method. Similarly, other step(s) of the method may be practiced in whole or in part at separate times and places. Accordingly, the present inventors also contemplate as their invention a method that contains fewer steps, particularly only steps (b)-(e).

In one aspect of the invention, the foregoing methods use at least three, at least four, at least five or at least six or more analytes that are measured or their levels determined in a biological sample drawn from a subject or patient. In another aspect, the foregoing methods involve the assessment or prediction of the presence or absence of a given disease, such a solid tissue cancers, including but not limited to breast cancer, prostate cancer and lung cancer.

In some embodiments, the meta-variable is age. In certain embodiments, the meta-variable is selected from the groups consisting of: pre, peri and post menopausal status, pubescence, body mass, geographic location of the source of the sample, body fat percent, race or racial mix or ethnicity, species or era (or range) of period of time.

In another embodiment, the "comparing" step as described herein involves the use of a correlation method selected the techniques including, but not limited to clustering, neighborhood search, regression or wavelet analysis methods. And, optionally may include the use of an incongruent training set model. Such incongruent training set modules may be used, as appropriate, with any of the inventive methods, such as in connection with the steps of transforming, comparing and determining that may be repeated with a second training set model capable of identifying non-disease conditions in the subject's population that partially mimic the serum analyte changes in the disease state but are not caused by the disease state as opposed to the conditions or pathologies of the disease itself. Thus, a related embodiment includes a second training set model and the evaluation and prediction of disease for three states: non-disease, non-disease condition that partially mimic the disease state, and the disease state.

In another aspect of the invention, the inventive methods are computer implemented through the use of microprocessor, and, optionally, further comprise the step of outputting a score in a form that is useful to a healthcare practitioner, such as a physician who is making a disease diagnosis.

Certain embodiments of the invention utilize mathematical methods for normalization, and smoothing of irregularities or noncontiguous distributions of the concentrations that include the use of a logarithm of the ratios of the measured concentrations and the age adjusted mean values of the concentrations of the proteins for the non-disease and disease states for which the individual sample is predictive and the ratio of the concentrations of the proteins for the non-disease and disease states, such that the distribution of the resultant new independent variable to be used in the correlation is compressed to aid the correlation calculation.

In another aspect of the invention, the relationship between the independent variables and the meta-variable encompasses population distribution characteristics of the independent variables associated with the degree of nonlinearity of the relationship between the states of disease and non-disease, one or more groups (either Gaussian or non-Gaussian), group mean values, group average values, group median values and group dynamic range values.

Certain embodiments of the invention include an adjustment to the training set model to weight the influence of the individual biomarkers based upon conventional (or specialized) knowledge of the individual biomarkers' up or down regulation characteristics, such as sub-groupings or degree of non-linearity, in the course of disease progression in a typical subject in the relevant population.

Certain other embodiments include an adjustment to the training set model to weight the influence of the individual biomarkers based upon conventional (or specialized) knowledge of the bi-marker plane topology instabilities on sufficient of the bi-marker planes to significantly change the risk score or disease state prediction, where those instabilities are caused by steep slopes or deep peaks or valleys in the topology of each bi-marker plane.

In other embodiments, the training set model is adjusted to weight the influence of the individual biomarkers based upon conventional (or specialized) knowledge of the biomarker assay uncertainties, such as the uncertainties that can occur at very low or very high levels on the assay results curve.

In another aspect of the invention, an incongruent training set model is used to adjust or correct individual blind samples that show instabilities in outcome prediction due to topology instabilities on enough of the bi-marker planes to significantly change the risk score for a given blind sample, where instabilities are caused by steep slopes or deep peaks or valleys in the topology of a bi-marker plane.

Another embodiment of the relates to more personalized medicine approaches to diagnosis and therapy in which the baseline values of the individual protein (or other analyte, such as metabolite) concentrations are determined for a subject over a period of time including a period of time when the subject is in the non-disease state rather than the population value for the disease for which a prediction of the presence of disease or its diagnosis is desired.

Yet another aspect of the invention relates to the measurement of low abundance biomarkers, including signaling proteins, that include at least one biomarker in each of at least three of the categories that include immune system inflammatory markers, tumor anti-angiogenesis markers, cell apoptosis markers, vascularization proteins associated markers, and tissue markers. In an embodiment of the invention, the low abundance biomarkers are very low abundance proteins with concentration levels below about 1 pg/ml in samples drawn from at least about 20 percent of the relevant population for a given subject.

Another embodiment of the invention involves the determination of the concentrations in a biological sample of at least three biomarkers selected from categories that include immune system inflammatory markers, tumor anti-angiogenesis markers, cell apoptosis markers, vascularization proteins and tissue markers, where any one or more of the at least three biomarkers other than the tissue markers are low abundance proteins with determined concentrations below about 1 pg/ml for at least about 20% of the relevant population for a given subject in a subpopulation that has the disease for which a diagnosis or prediction of the likelihood of disease is desired.

In a preferred embodiment, the disease is cancer, and more particularly, a solid tumor.

In other embodiments, at least two or more, at least three or more, at least four or more, at least five or more, at least six or more, at least seven or more, at least eight or more, at least nine or more or at least ten or more biomarkers are evaluated (or have levels determined).

Yet another aspect of the invention involves the evaluation or analyses in which the concentration values for at least one of the determined (or measured) analytes are below the LOD, where the concentration value for such analyte(s) is determined by a straight line or other appropriate standard curve fitting method between the LOD and the lowest reading for the analyte. Preferably, no analyte is given a zero or negative value, and no analyte is given a value less than about the lowest accepted value for that analyte in similar samples.

In other of its embodiments, the invention involves a diagnostic kit with reagents for the detection of one or more analytes, two or more analytes, three or more analytes, four or more analytes, five or more analytes, six or more analytes, seven or more analytes, eight or more analytes, nine or more analytes or ten or more analytes that are below their LOD.

Another embodiment of the invention involves computer systems and microprocessor-mediated equipment and systems useful to accomplish any of the methods, diagnostic predictions and analyses described herein, including any one or more of the steps discussed in this specification.

DESCRIPTION OF THE DRAWINGS

The following figures, which are described below and which are incorporated in and constitute a part of the specification, illustrate exemplary embodiments according to the disclosure and are not to be considered limiting of the scope of the invention, for the invention may admit to other equally effective embodiments. The figures are not necessarily to scale, and certain features and certain views of the figures may be shown exaggerated in scale or in schematic in the interest of clarity and conciseness.

FIG. 1 is a flow chart that represents the process of constructing the Training Set Model (or diagnostic model) and then producing diagnostic scores for blind samples that assess rick of having the disease state or non-diseased state.

Figure 2:
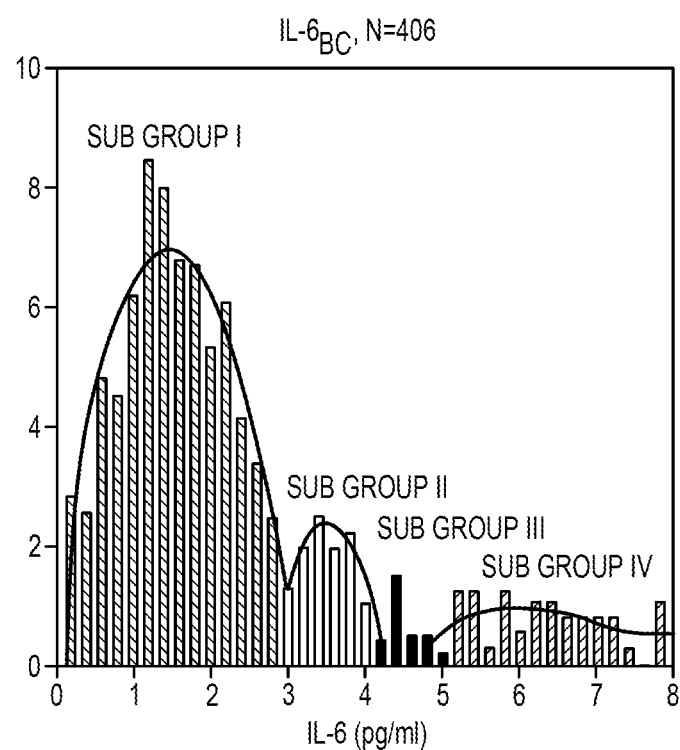
FIG. 2 represents a typical population distribution, in this case for the cytokine Interleukin 6.

Table 1 shows the stability calculation and figure of merit for Algorithm I from a clinical study Table 2 shows the results of a preclinical study on 868 women for breast cancer.

Table 3 shows relative predictive power for various correlation methods for the 868 women breast cancer study.

Table 4 shows the results of a preclinical study on 107 women for ovarian cancer.

Table 5 shows the results of a preclinical study on 259 men for prostate cancer.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed below are merely representative and do not limit the scope of the invention.

In a preferred embodiment, the present invention relates to a method for diagnosing a disease, as described in greater detail below. By way of an introduction to what follows, the method overall utilizes measured concentrations of predetermined analytes in a blind sample from a patient for whom a predictive diagnosis is desired as to having the disease or not. According to the methods of the invention, each analyte concentration is converted into a pseudo-concentration based on the use of at least one selected meta-variable that is associated with the patient, which meta-variable also varies in a selected population associated with the patient. In that selected population, the concentrations are measured for the same predetermined analytes for members of the population who are known either to have or not to have the disease. For the purpose of disease diagnosis, the pseudo-concentrations are processed by the methods and algorithms described below. The processed pseudo-concentration values are compared to a diagnostic model (or training set model) of pseudo-concentrations determined and similarly processed for members of the population who are known to have or not to have the disease. Ultimately, a determination is made as to whether or not the evaluation of the sample taken from the patient to be indicates a patient's status as being in the population group having a non-diseased or disease state. This determination can be viewed, for example, as a result that is outputted from a computerized system for use by health care providers.

The process stepwise is shown in the flow chart FIG. 1. Construction of the Training Set Model is done first and its end product enables producing diagnostic results for unknown patient samples, termed blind samples, as the correct diagnosis is not known at the time of analysis for these blind samples. In general, the present invention provides a risk score to a health care provider who then considers this score along with other patient factors to make a medical judgment about the presence or absence of a given disease state.

Definitions

"Analytical Sensitivity" is defined as three standard deviations above the zero calibrator. Diagnostic representations are not considered accurate for concentrations below this level. Thus clinically relevant concentrations below this level are not considered accurate and are not used for diagnostic purposes in the clinical lab.

Figure 3:
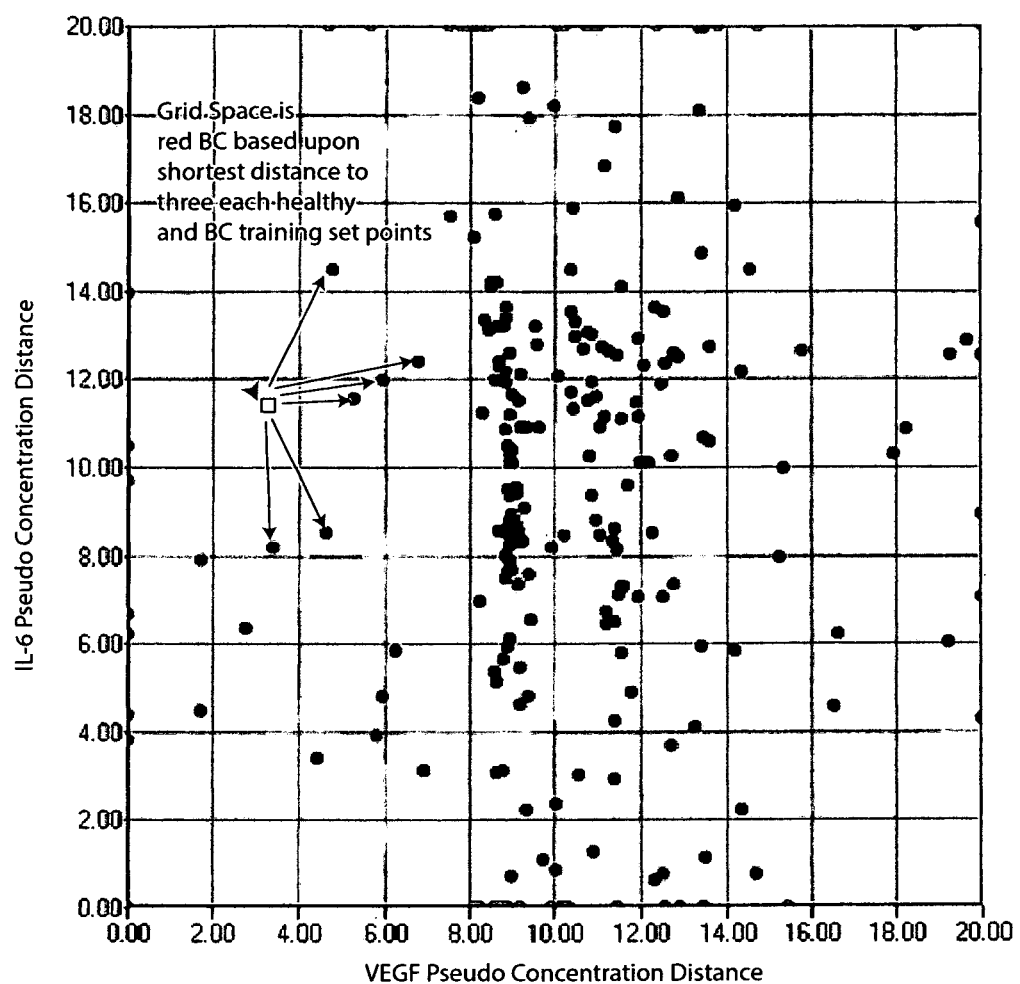
FIG. 3 represents a bi-marker plane for one of the ten such planes showing pseudo-concentrations of two of the bio-markers used in the diagnostic method.

"Bi-marker" is a set of two of the pseudo-concentrations that are normalized and functionally related to a meta-variable's variation with respect to the biological transition from a non-disease to a disease state when plotted in a two axis graph (or grid), as shown, for example, in FIG. 3, and referred to below as "bi-marker planes."

"Biological Sample" means tissue or bodily fluid, such as blood or plasma, that is drawn from a subject and from which the concentrations or levels of diagnostically informative analytes (also referred to as markers or biomarkers) may be determined.

"Biomarker" or "Marker" means a biological constituent of a subject's biological sample, which is typically a protein or metabolomic analyte measured in a bodily fluid such as a blood serum protein. Examples include cytokines, tumor markers, and the like.

"Blind Sample" is a biological sample drawn from a subject without a known diagnosis of a given disease, and for whom a prediction about the presence or absence of that disease is desired.

"Limit of Detection" (LOD) is defined as a concentration value 2 standard deviations above the value of the "zero" concentration calibrator. Usually the zero calibrator is run in 20 or more replicates to get an accurate representation of the standard deviation of the measurement. Concentration determinations below this level are considered as zero or not present for example, for a viral or bacterial detection. For purposes of the present invention, 1.5 standard deviations may be used when samples are run in duplicate, although the use of 20 replicates is preferred. Diagnostic representations requiring a concentration number are not rendered below this level.

"Low Abundance Proteins" are proteins in serum at very low levels. The definition of this level is not clearly defined in the literature but as used in this specification, the level would be less than about 1 picogram/milliliter in blood serum or plasma and other body fluids from which samples are drawn.

"Meta-variable" means information that is characteristic of a given subject, other than the concentrations or levels of analytes and biomarkers, but which is not necessarily individualized or unique to that subject. Examples of such meta-variables include, but are not limited to, a subject's age, menopausal status (pre-, peri- and post-) and other conditions and characteristics such as pubescence, body mass, geographic location or region of the patient's residence, geographic source of the biological sample, body fat percent, age, race or racial mix, or era of time.

"Population Distribution" means the range of concentrations of a particular analyte in the biological samples of a given population of subjects. A specific "population" means, but is not limited to: individuals selected from a geographic region, a particular race, or a particular gender. And the population distribution characteristic selected for use as described in this application further contemplates the use of two distinct subpopulations within that larger defined population, which are members of the population who have been diagnosed as having a given disease state (disease subpopulation) and not having the disease state (non-disease subpopulation). The population can be whatever group in which a disease prediction is desired. Moreover, it is contemplated that appropriate populations include those subjects having a disease that has advanced to a particular clinical stage relative to other stages of progression for a given disease.

"Population Distribution Characteristics" are determinable within the population distribution of a biomarker, such as the mean value of concentration of a particular analyte, or its median concentration value, or the dynamic range of concentration, or how the population distribution falls into groups that are recognizable as distinct peaks as the degree of up or down regulation of various biomarkers and meta-variables of interest are affected by the onset and progression of a disease as a patient experiences a biological transition or progression from the non-disease to disease state.

"Predictive Power" means the average of sensitivity and specificity for a diagnostic assay or test.

"Pseudo-concentration" means a substitute or replacement value for the concentration of a measured biomarker and is, in effect, a new independent variable that may be used in a diagnostic correlation analysis. The pseudo-concentration is related to and computed from the concentration of measured biomarker analytes, where such analytes have an inherent predictive power for a given disease state. The pseudo-concentration is computed using a meta-variable adjusted population distribution characteristic of interest to transform the actual measured concentration of the predictive biomarker for a given patient for whom a diagnosis is desired.

"Topology Instability" is an area on the grids of most or all of the bi-marker planes where all or most of the points in the area are sitting on steep slope sections of the topology. The topology is the shape of the multi-dimensional correlation computation that takes all of the measured independent variables (that is, the determined biomarker concentrations) and the meta-variable into account. This topology, for a single value of the meta-variable, is at least five dimensions for a five biomarker measurement (it can be more). The topology also shifts in shape as the meta-variable changes in value. This multi-dimensional topology can be visualized by eye in pieces by taking ten biplane slices through the topology. This renders the calculated disease scores "at risk" of being wrong due to measurement noise. The score can be derived by weighting the individual bi-marker plots for predictive power to the disease and non-disease state, and by taking into account other factors such as topology measurement instability and simple measurement error. The score range is arbitrary, as would be known to persons skilled in the field, and the value represents a percent probability of the patient being in the disease or non-disease state.

"Training Set" is a group of patients (200 or more, typically, to achieve statistical significance) with known biomarker concentrations, known meta-variable values and known diagnosis. The training set is used to determine the axes values "pseudo-concentrations" of the "bi-marker" planes as well as score grid points from the cluster analysis that will be used to score individual blind samples.

"Training Set Model" is an algorithm or group of algorithms constructed from the training set that allows assessment of blind samples regarding the predictive outcome as to the probability that a subject (or patient) has a disease or does not have the disease. And the "training set model" is then used to compute the scores for blind samples for clinical and diagnostic purposes. For this purpose, a score is provided over an arbitrary range that indicates percent likelihood of disease or not-disease or some other readout that may be preferred by a healthcare provider who is developing a diagnosis for a patient.

"Incongruent Training Set Model" (or "Secondary Algorithm") is a secondary training set model that uses a different phenomenological data reduction method such that individual points on the grids of the bi-marker planes are not likely to be unstable in both the primary correlation training set model and this secondary algorithm.

Discussion

Certain aspects of the invention including defined terms are discussed below in greater detail as guidance to persons skilled in the art in practicing the present invention.

Meta-Variables:

The claimed invention relates, in part, to improved diagnostic methods for correlative diagnostic assays using meta-variables. Such meta-variables may contribute to predictive power for diagnostic purposes when they exhibit a significant range of variation in "normal" values in members of a population that are known either to have or not have a given disease. As described in this specification, meta-variables are used to transform or convert measured analytes levels to "pseudo-concentrations." It is contemplated that the levels or concentrations of various analytes may be measured or determined by techniques known to persons of skill in the diagnostic field.

A meta-variable is likely to be relatively more informative when it has a physiological or physicochemical connection with the biological status of a subject that reflects a change over time as the disease state develops, even though that meta-variable is not in and of itself particularly predictive. For example, body mass index (BMI) is an available meta-variable, and body mass itself affects various signaling protein levels in cardiac diseases. In the methods of the present invention, BMI may be significantly more useful in a predictive assay when it is used as a meta-variable rather than as another independent variable, such as independent variables like the measured levels of various circulating blood proteins. The present invention is based, in part, on the discovery that the variation of body mass throughout a population associated with a human subject is further associated with determinable population distribution patterns of measured blood serum protein levels. These protein (or biomarker) levels are the independent variables measured for diagnostic purposes as a given subject experiences a biological transition (or progression) from a state of being non-diseased to diseased.

Similarly, the present inventors have shown a subject's age in diagnosing disease, for example, cancer, when used on its own as an independent variable together with measured analyte levels in conventional correlation methods is not clinically predictive. However, when age is used as a meta-variable according to the methods of the present invention, its use does improve diagnostic accuracy.

In general, a meta-variable as defined and described in this application will be predictive for diagnostic purposes if the population distribution characteristics of a measured analyte show significant functional separation (or variance) when comparing non-disease and disease subjects. This functional separation means that the relationship of the meta-variable (age) and the population characteristic of interest (population mean value) for the disease state and non-disease state are substantially different.

The graph in FIG. 2 shows the population distribution of IL-6, notably including four distinct population subgroups labeled I through IV, which reflects immune responses to cancer progression. The higher concentration groups are believed to be the result of a stronger immune response to immune stimuli such as infection, wounds, allergies, and of course cancer, and the highest group (IV) shows a decided non-linear reaction to the IL 6 these stimuli. These population distribution characteristics and such groupings of measured analytes can be used to improve predictive power of a training set diagnostic model.

The meta-variable diagnostic methods of the present invention are based on research that included an evaluation of about 868 patient samples. In those samples, the concentrations of five probative low level signaling proteins (PSA, IL-6, IL-8 TNFα and VEGF) were measured in subjects diagnosed clinically as having or not having breast cancer. The protein (or analyte) levels are classic independent variables for disease diagnostic testing.

The inventors also obtained age information on each of these subjects. A classic logistic regression analysis of five biomarkers achieved about 82% predictive power, and the use of age as a sixth independent variable in this analytical method was found to produce negligible improvement in predictive power. A data clustering method using only the determined biomarkers also achieved a slightly higher predictive power of about 88%. Again, using age as an independent variable was not substantially more predictive.

Similarly, the use of classic cluster analysis, with the concentration values converted to logarithms, achieved a predictive power of about 92%, but the use of age as an independent variable added less than 0.5% to that predictive power. In this kind of analysis, as is known, the logarithm of the sample concentrations was used because these analyte concentrations can spread over four or more logs of dynamic range. It is also known that the blood levels of the five analytes in patients with cancer tend to progress to highly elevated concentrations, but not always. Thus, this approach brings the points in the training set model on the multi-dimensional cluster plots into close proximity obviating the tendency to over-sample cluster points at low concentrations. This logarithmic method of compression is commonly used, as it reduces spacing bias.

The present inventors established that an individual subject's age, for example, can be used to create what is referred to in this specification as a meta-variable. The meta-variable is used in turn to create new independent variables that are referred to in this specification as pseudo-concentrations, which are computed from the population distribution characteristics of the measured independent variables (in this case, protein concentrations). Doing so, as discussed in greater detail in this specification, produced about 97% to over 100% predictive power in two analytical models. For purposes of this application, a predictive power that is over 100% means that the "disease" and "non-disease" states are separated by a significant gap in correlation scores.

Population Distribution Characteristics:

Examples of population distribution characteristics that have been found by the present inventors to be probative, when age is selected as a meta-variable, are the mean concentration value of each measured analyte for patients either having or not having the disease; and the median concentration value for subgroupings of concentration values for segregated age groups (or for the population as a whole) for disease and non-disease patient groups as shown in FIG. 2. The subgroupings shown in the population distribution plot are mathematically adjusted differently, that is, the high level up-regulated concentrations in the group above 5 pg/ml are highly compressed. These relationships produced new age-based independent variables that were then used directly in the cluster analysis rather than the actual concentration levels of measure biomarker analytes.

The mean values of the concentrations are determined versus age for patients diagnosed as being in the non-disease and disease state. This is called the age adjusted mean for each state. The pseudo-concentration values are computed from these mean values and the actual concentration for the patient using Equation 1 (which is described in the subsection relating to pseudo-concentrations).

As is common with multi-independent variable correlation analysis, the multiple independent variables are paired in multi-dimensional plots for the basis of the classic cluster proximity analysis. Also, these variables are often compressed in order to accommodate the relatively large dynamic range spreads of the measured variables (that is, the analytes). In this case, we describe here a method where the independent variables are "pseudo-concentration" values based upon age or other meta-variables and the actual concentrations. It is contemplated that persons skilled in the art will readily be able to identify and select population distribution characteristics that improve predictive power.
Pseudo-Concentrations:

To extract the predictive power of a patient's age, which itself can also be treated as an independent variable in other diagnostic approaches, the present inventors used age as a meta-variable to compute "pseudo-concentrations" that are then used as substitutes for the actual measured concentrations of the determined analytes. It is important that the meta-variable must have separation, in a given population of interest, between the non-disease state and disease state to extract its predictive power for all meta-variable values, for example, age in the case of breast cancer. By "separation" is meant that the observed relationship between a population characteristic for subjects in non-disease and disease subpopulations be different for a particular meta-variable. This can be determined empirically by measurements and calculations. And a population of interest is determined by the nature of the desired predictive outcome group, it may be, but is not limited to: a geographic region such as, for example, the continental United State; a particular race or ethnic grouping; or a particular gender, such as, for example, females.

In practicing the method according to the present invention for the prediction of breast cancer disease, the concentrations of five or six very low level signaling proteins preferably are the independent variables for the diagnostic correlation. Each of the five biomarkers was measured, and their variations with age were determined in the test population, which was women aged 35 to 80, one half were healthy and one half were diagnosed with breast cancer. While a subject within a population generally is considered to have a disease or not, the biomarker levels determined for a single subject change as that subject's disease progresses, and not all subjects have the same level of the biomarkers before and during the onset and progression of their disease through its various phases. Thus, the population distribution characteristics reflect normal variability of a biomarker in a subpopulation in a non-disease state as well as the normal variability of a biomarker in a subpopulation in a disease state.

The population distribution characteristics in this case were: 1) mean values versus age for the non-diseased and diseased state (in this case, cancer); and the 2) degree and non-linearity of up-regulation of the biomarker going from non-disease to disease. For example, the up-regulation of Interleukin 6 is shown in FIG. 2 as this cytokine's level reflects the subjects' reactions to an immune challenge resulting from the cancer. IL-6 is a known pro-inflammatory responder that up-regulates as a signal to the immune system to turn up its general response. The four separate groupings show different levels of up-regulation. These levels are taken into account when the pseudo-concentrations are calculated. For example, the degree of data compression in going from actual compression to pseudo-concentration varies by grouping location and is very severe for the upper group 4.

In order to accomplish the foregoing, one must measure the population with equal numbers of subjects having a non-disease and disease state. The size of this training set optimally is determined by the number of biomarkers used. The preferred size is where the training set model's predictive power is within about 95% accurate for a similar or larger blind population set. One can then determine the age adjusted mean values of these two states and can see the effect of the disease on degree of up or down regulation of the biomarker.

FIG. 2 shows the population distribution characteristic of one biomarker, IL-6, as the immune system up-regulates the protein when the immune system is challenged by the presence of cancer or other pro-inflammatory condition. The translation from measured concentration to pseudo-concentration involves normalizing the concentration to the age adjusted means for again non-disease and disease populations, and compressing the dynamic range of the measured concentration values. The highly scattered outlying concentrations in the grouping above 5 pg/ml that extend up to as high as 100 pg/ml for example are highly compressed. This improves predictive power. The result is a new independent variable, referred to in this application as a pseudo-concentration, that is unit-less, normalized and reflects, in one preferred embodiment, the age variations in the population distributions of the biomarkers.

A relationship that includes age adjusted mean for non-disease and disease and the actual patient sample concentration of the following form is used:

$$\text{pseudo-concentration} \propto \text{natural logarithm } ((C_i/C_{(o\ or\ h)})-(C_h/C_c))^2 \quad \text{Equation 1:}$$

Where:
- $C_i$=measured concentration of the actual patient's analyte
- $C_{(c\ or\ h)}$=patient age adjusted concentration of this patient analyte; the value is adjusted for whether the patient is a non-disease or disease state.
- $C_h$=patient age adjusted mean concentration of non-disease patients' analyte
- $C_c$=patient age adjusted mean concentration of disease patients' analyte.

This Equation 1 is designed to adjust compression and expansion depending on the up-regulation grouping, see the peaks, for example, in FIG. 2. The formula above for Pseudo-concentration accomplishes this requirement; however, many other forms of this equation can be implemented as will be apparent to persons skilled in the art. For example, $C_i$, $C_h$ and $C_c$ could be directly concentrations or concentration distances from the mean, medium or distance from sub group medians or dynamic range edges as discussed above.

Pseudo-concentrations (unit-less and thus not concentrations or levels) are then used in the correlation cluster multidimensional plot for analysis. Also all of the plots are normalized to common characteristics of the population distribution; age mean values of non-disease and disease (age adjusted or not), median value, or dynamic range of sub groupings. These methods can yield improvements in predictive power of 5 or more percentage points.

The case for individualized medicine is gaining in popularity and efficacy. It is also contemplated that the disease prediction methods described above can be personalized by substituting population distribution characteristics developed and described in these patents for the non-disease condition with the non-disease baseline measurements for an individual. In other words the $C_h$ value in the equation above would be the actual base line value for the individual patient and not the population mean value for the non-disease state. The disease assessment would correspondingly then be based upon the individual's transition from these measured non-disease characteristics to the disease characteristics that are indicative of the general population.

Bi-Marker Planes:

For an analysis using five biomarkers (and one meta-variable), there will be ten such bi-marker planes. The plot in FIG. 3 shows red disease and yellow non-disease grid points. The training set samples, using the independent measured variables (concentrations) and the meta-variable (age) determine the age population characteristics, calculate the pseudo-concentration distances on the axes, and these pseudo-concentrations are applied to each of the ten bi-marker planes. The plot is divided into 2,000 grids on each axis for 40,000 grid points total.

The determination of whether a grid point is disease or non-disease is computed by determining the distance from each individual grid point to nearest measured data points for the training set samples. FIG. 3 provides an example, and in this case the two biomarkers are IL-6 and VEGF and the meta-variable used is age. The ordinate and abscissa are both pseudo-concentrations determined as described above. The meta-variable and the measured independent variables are thus embedded in the pseudo-concentration on these plots. The grid points are each valued as non-disease and disease and given a corresponding numerical score (for example, +1 and −1, although the actual numbers are arbitrary). This score is determined by the calculated distance to two training set data points, non-disease or disease. The shortest distance determines this score. The number of training set samples can be varied to make this distance determination (for example, about 4 to 6) see FIG. 3. A relatively low number of compared samples, will likely render a relatively reduced predictive power. Likewise an increased number of compared samples can reduce the predictive power as the "reach" of the grid point extend to far into non-local regions on the topology. The best number is determined by experimental calculation.

The preferred number of compared sample points is where the training set model most agrees with the actual diagnosis. FIG. 3 shows this computation process for two biomarkers, IL-6 and VEFG. The unknown grid point (small square box at around 12.00 on the y-axis and about 4.00 on the x-axis on the plane) is assigned the non-disease or disease state by determining its distance to, in this case, the three closest training set data points for each non-disease and disease. These distances are added up and then the grid point is assigned the appropriate state non-disease or disease (computation score of +1 or −1 respectively). Any blind sample diagnosed at some future point will be assigned the state score based upon where it falls on this grid. Each blind sample will also be scored for all bi-marker planes. The total number of training set samples can be at least 200 and more.

The determination of the overall cancer score for blind samples is determined from all of the bi-marker planes by using the individual grid point determination for the individual sample multiplied by the overall predictive power for the individual bi-marker plane. The individual blind sample grid point value (+1 or −1 for example) is multiplied by the predictive power (or sensitivity) of the individual bi-marker plane. All ten planes are then summed together. Typical linear and/or square root of the sum of the squares methods are used to produce a final overall score for all of the bi-marker planes. The scores are normalized and shifted to produce scores from 0 to 200, which is the output used by a health care provider. This range is arbitrary.

Larger sets of bi-marker planes can be constructed from the same group of biomarkers by mathematically manipulating them. These larger bi-marker sets may well have more predictive power or they may constitute an incongruent training set model (or secondary algorithm) for further improvements in predictive power. For example using the ratios of 5 biomarkers concentrations—rather than the concentrations themselves—for the construction of each pseudo-concentration will create 10 pseudo-concentration values and 45 bi-marker planes. A construction of pseudo-concentrations and bi-marker planes may well be more predictive but likely will require larger training sets to accurately correlate with the general population. One could also use, for example, the ratio of each concentration divided by 1 minus another concentration value. A person skilled in the art can readily determine whether these alternate methods for conditioning the data for the multi-dimensional cluster analysis have better predictive power by testing the method(s) for predictive power with blind sample sets.

In order to further improve predictive power, these age or grouping-adjusted concentrations are conditioned to normalize them and reduce or eliminate spacing bias in the clustering across the multidimensional grouped marker plots for the cluster proximity analysis. See FIG. 3, which presents the bi-marker plane for IL-6 and VEGF. There are ten of these planes for the five-biomarker breast cancer test panel. In this case, the calculated pseudo-concentration values are normalized and shifted to produce arbitrary values between zero and twenty with outlier highly up-regulated concentrations being highly compressed.

Each of the bi-marker projections of the multi-dimensional marker planes on the same normalized spacing over the concentrations from the age/grouping analysis are compressed and normalized against the age adjusted means as well as age (or whole populations) adjusted sub-groupings.

Improvements in Predictive Power of the Training Set Model Using Adjustable Bi-Marker Plane Influence Levels:

Typically the bi-marker plane will be scored with binary numbers for non-disease and disease (for example, +1, and −1). The pseudo-concentration method described herein is amenable to further improvements in predictive power by selectively adjusting the influence levels of these two binary numbers. The methods below are developed in the training set model and once set are fixed in the model.

Figure 4:
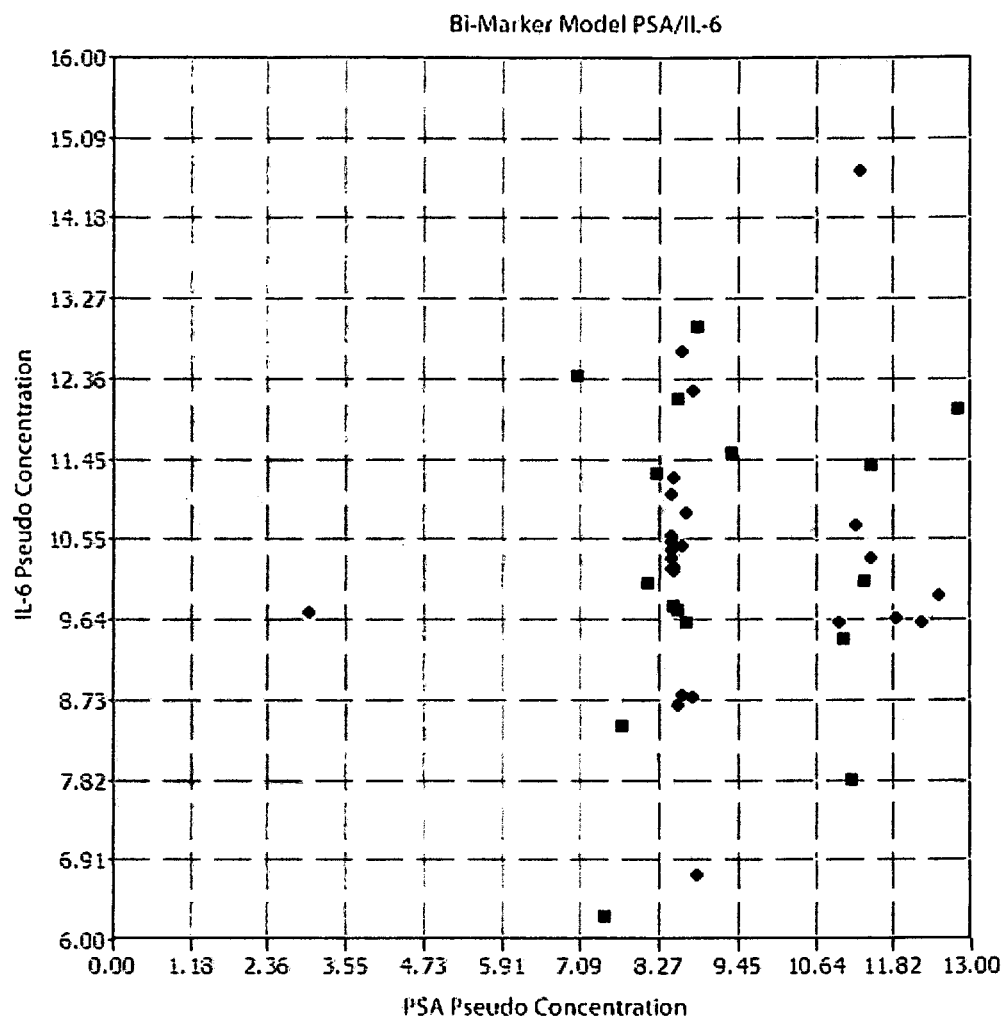
FIG. 4 shows a bi-marker plane with training set data points.
Figure 5:
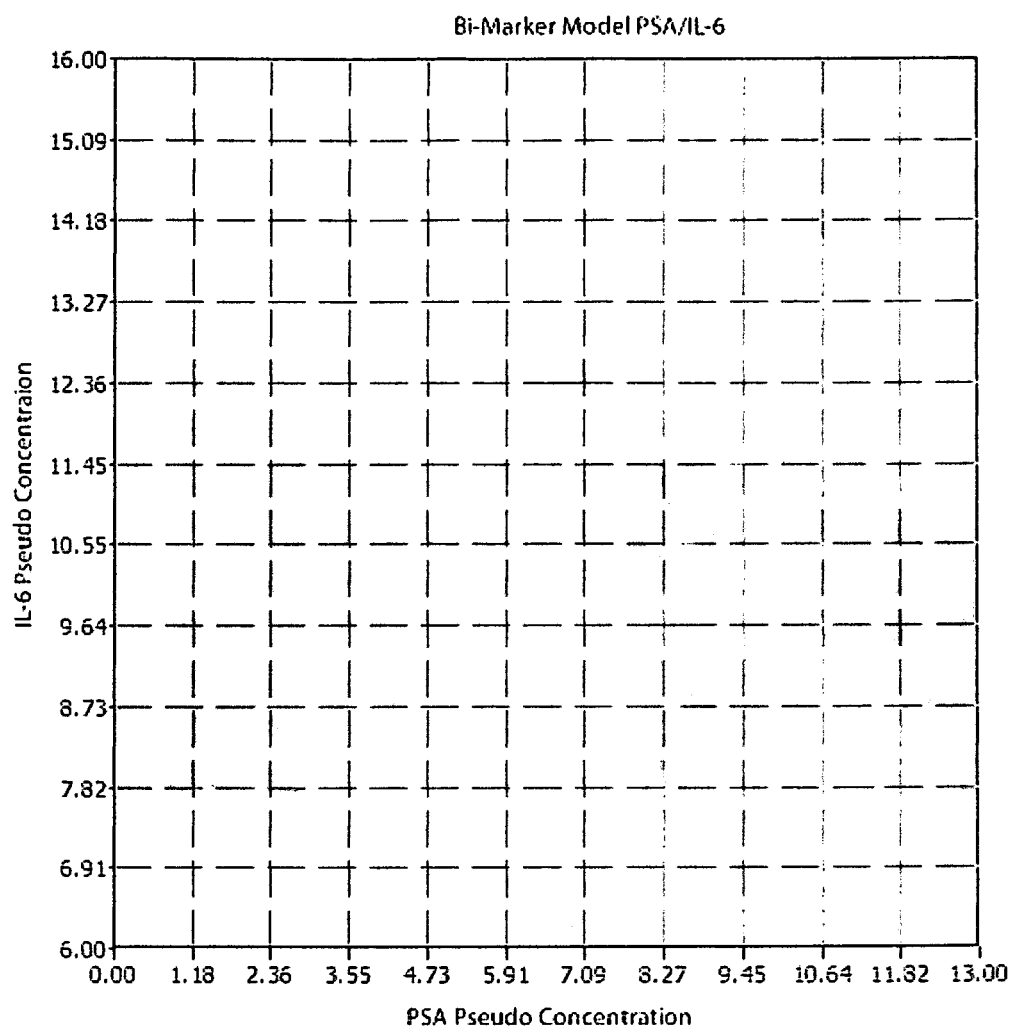
FIG. 5 shows a bi-marker plane without the training set data points.

FIGS. 4 and 5 below shows the projections of one bi-marker plane for the case of five biomarkers used to predict presence of the disease state, in this case breast cancer using the five markers; IL-6, IL-8, TNFα, VEGF and PSA. FIG. 4 shows the training set model with the data used to score the grid points on the plot by the cluster search analysis. FIG. 5 shows the training set model without the data. This constitutes the training set model. The training set data used for creating the model are not needed as each of the 40,000 grid points are scored and a blind sample is scored by where it lands on the grid. The topology shows red positive for cancer and the blue are negative for cancer. In computing the overall score in this case, the non-disease grid points are set at +1 and the disease (cancer) grid points are set at −1. Each bi-marker in this five-biomarker example is analyzed in a five orthogonal space of which FIG. 5 is one projection of two dimensions. On this plot are shown the topology of the various sub groupings of immune system response. In this case the all grid spots (2000×2000 or 40,000 in this case) are scored in the usual way and the value assigned is −1 for disease state positive (breast cancer) and non-disease is +1. This bi-marker plane is normalized by pseudo concentration spacing and for the meta-variable age as noted above.

Figure 6:
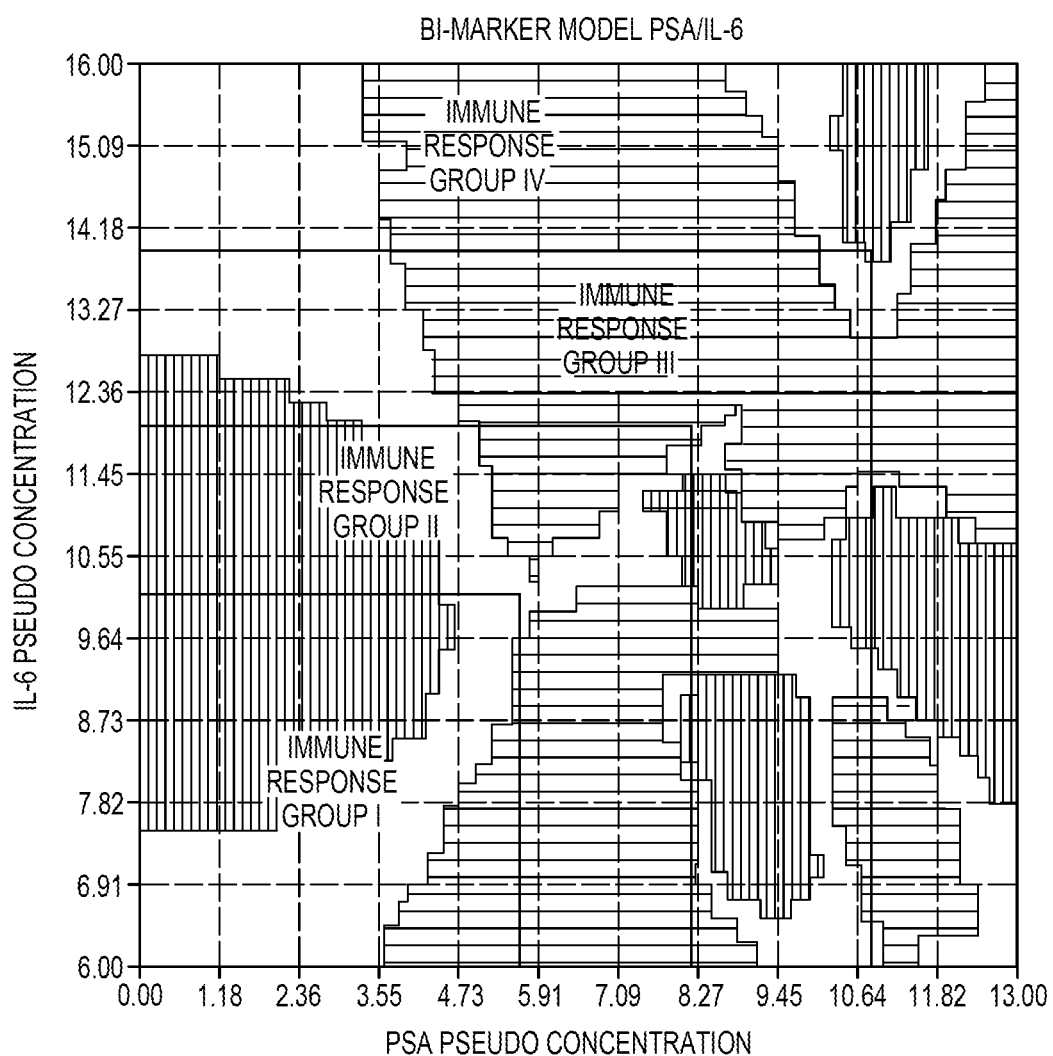
FIG. 6 shows a bi-marker plane with shaded area where influence is lowered for immune system response.

FIG. 6 shows the same bi-marker model and additionally the immune response groupings (see FIG. 2) inside the grey areas. The grayed areas' influence is adjusted to reflect the fact that each grey blocked area has a somewhat different influence on the probability that the patient is non-disease or disease. This adjustment can be made either by human estimate with training set validation (did the adjustment yield corrected training set results), or by rigorous computer multi-variable incremental analysis. Two separate bi-marker planes are created for the two outcomes, which are the disease and non-disease states. In this case, blind data points in the Immune Response Group IV are much more likely to be disease and the influence would be increased (absolute value) slightly (for example, by changing the score from −1 to −1.1). The actual amount of this increment preferably would be determined by computer analysis or possibly by rigorous manual methods. This method is workable for the cluster search method of correlation analysis but other means could be used to the same effect. These methods of weighting the influence with respect to association of disease can produce an improvement in predictive power of about 1%. At predictive powers above 95% this is very significant.

Figure 7:
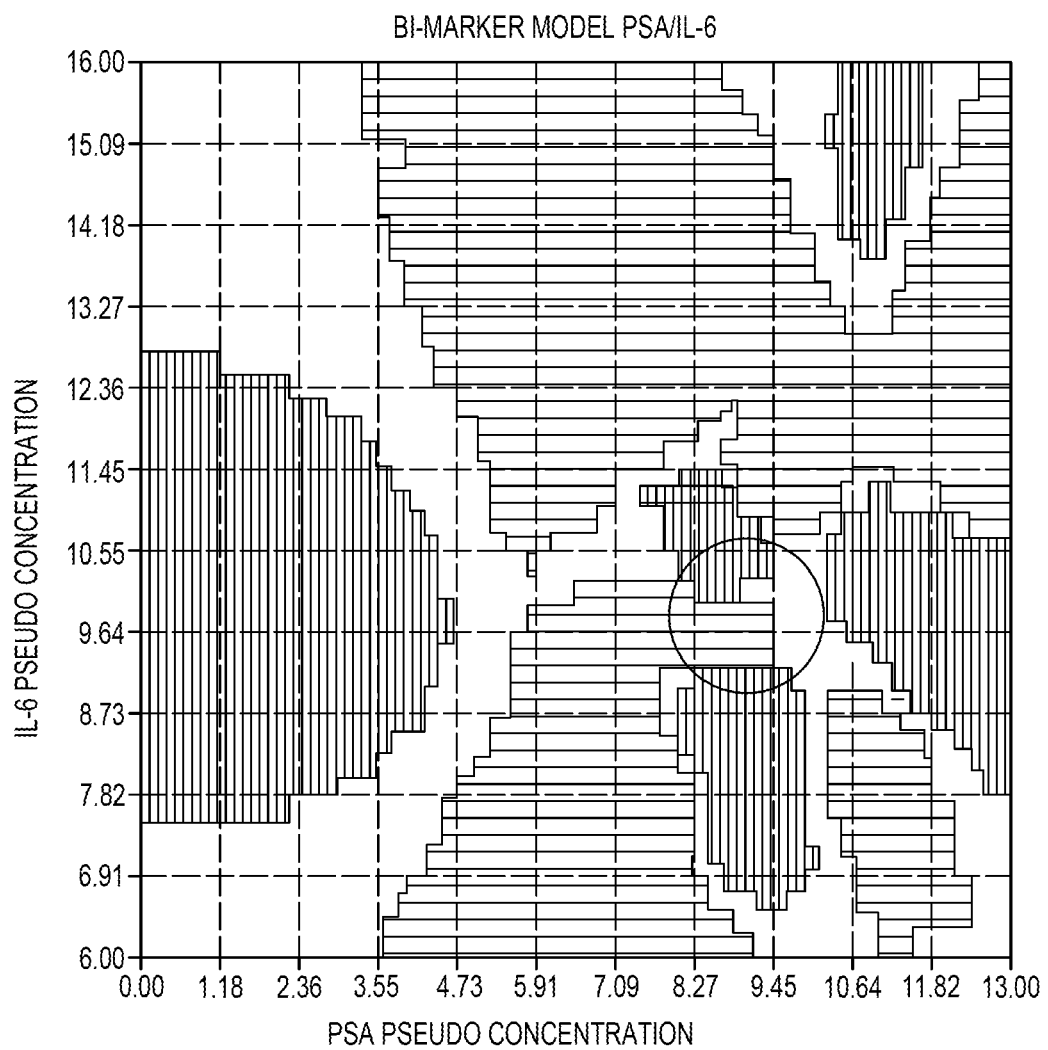
FIG. 7 shows a bi-marker plane with shaded area where influence is lowered for topology stability problems.

FIG. 7 shows again the same bi-marker plane with a grey area circled in a complex area of non-linear, rapidly changing disease vs. non-disease topology. Such areas can be identified by inserting test blind sample values with injected noise (say +/−10%) into the model and then inject a measured amount of noise. Most of these blind points will not change substantially in disease (here, cancer) score. Some grid points, however, may be found that jump dramatically from a non-disease to disease score after this kind of noise adjustment. These are areas where most or all of the bi-marker planes have rapidly changing topology that overlaps the multi-dimensional overall bi-marker planes. By careful reduction in influence in these areas, weighting can be increased in the few relevant bi-marker planes that the noisy datum sits on a broad plane without being near changing outcome boundaries. This method has been shown to correct erroneous predictions. In the case above the influence of the red, cancer areas would be shifted down (absolute value), for example, from −1.0 to −0.9. Or the blue non-disease areas would be shifted down from +1.0 to −0.9. The level of optimal shift could be determined by rigorous computer analysis.

Figure 8:
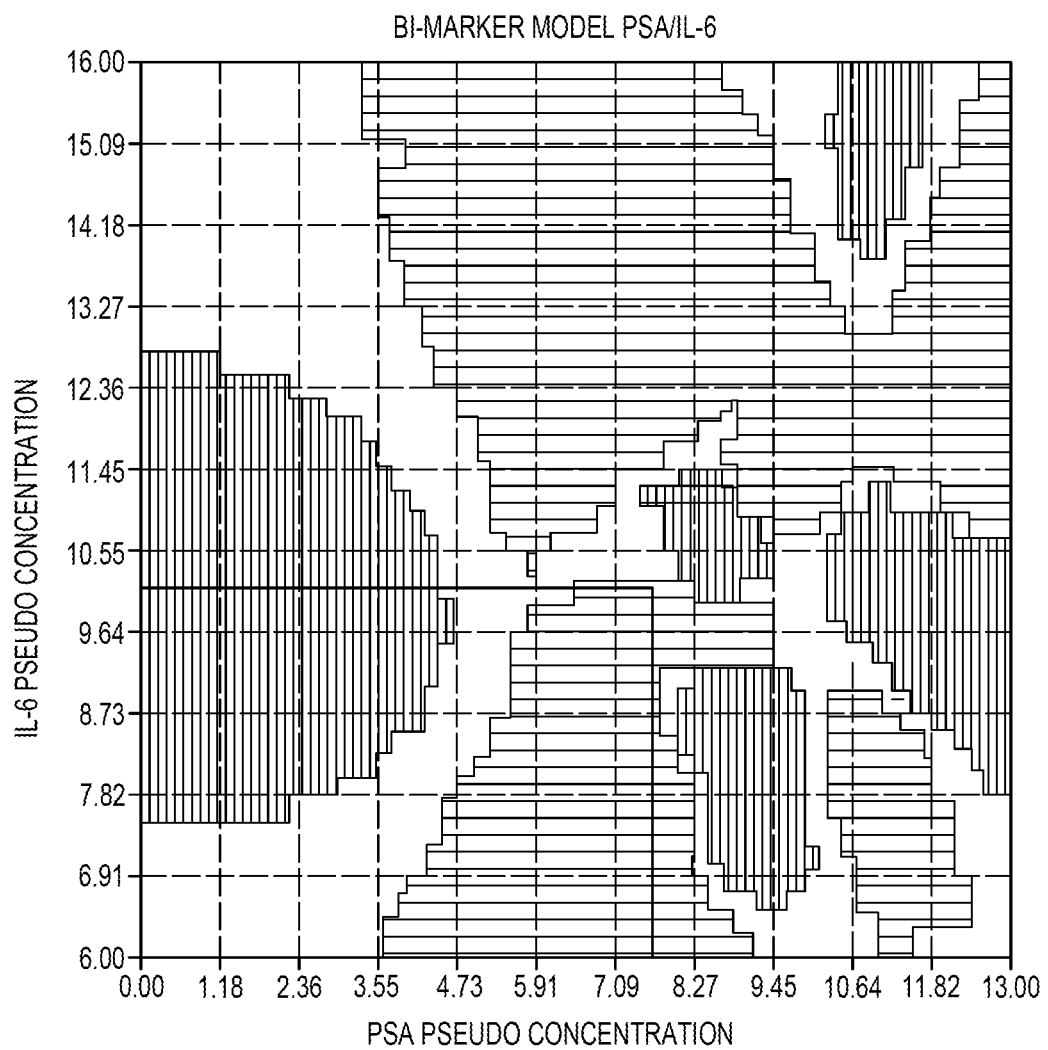
FIG. 8 shows a bi-marker plane with shaded area where influence is lowered for known assay measurement uncertainty.

Assay noise can affect the accuracy of the correlation analysis. This noise can be especially problematic at levels at or below the assay's limit of detection. This noise also can be mitigated by reducing the influence of measured points for individual biomarkers that are in these unstable zones. FIG. 8 again shows the bi-marker plane for PSA and IL-6 for a breast cancer panel. Areas within the grayed rectangular area at the bottom left of the figure are all below the traditional limit of detection (LOD) of the assay. Traditionally LOD is defined as two standard deviations of 20 zero calibrators plus the average of the value of the twenty zero calibrators. The statistical certainty for the values at this level are 95% within two standard deviations, and of course the measurement certainty goes down as the measured sample goes lower than the LOD. The data still may still have useful information but should be applied to the analysis with less influence. In this case, the influence on blind sample datum points within the grayed area are reduced, for example, from +1.0 to −0.9 for grid points of the training set model within the gray area. This increases the influence for datum points for this test sample that are above the limit of detection on their, other bi-marker planes.

The foregoing methods are complimentary and can be implemented in tandem, by combining the influence shifts.

Methods for Improving Predictive Power by Testing the Blind Samples for Instability:

Once the training set model is complete and fixed, it is used to calculate cancer scores for blind patient samples. The inventors use two preferred methods for producing cancer scores. The first, termed the linear method (CSl) takes the topology location score (+1 or −1) multiplied by the predictive power for that bi-marker plane. These are then added up and scaled and shifted to yield a score from 0 to 200. The second score, termed the q score (CSq) is calculated by using the square root of the sum of the squares on these same values. This second method accentuates difference in individual bi-marker score and is useful in the overall physician's ultimate diagnosis.

Topology instability does still remain in the bi-marker planes due to the highly non-linear nature of the clustering method of correlation and cannot be completely eliminated. The locations of these instabilities can be found by extensive and rigorous evaluation for computed cancer score of each grid point step-by-step wise incrementing the values of the pseudo-concentrations over each bi-marker plane. This would involve extensive computer calculations 40,000 grid points times 10 bi-marker planes times the number of bio-markers (2,000,000 calculations for 5 biomarkers). The unstable areas will be revealed by large swings in cancer scores at adjacent grid points. This also can be done less rigorously by a visual overlay of all ten bi-marker planes looking for areas of close transition from healthy to disease (for example, cancer, on approximately 5 or more of the planes. These visually found areas can then be verified by a lesser number of computer verification calculations.

According to another aspect of the present invention, a stability test and techniques involving injected noise can be applied to the blind data set. And an incongruent training set model can be used to arbitrate or correct cancer scores. For this aspect of the invention, a fixed level of noise is injected for each blind patient data set (for example, plus or minus 10%). If the blind sample set is about 100 patients, then the actual training set model computer run will be for 300 samples set with each in triplicate (the raw data plus noise and minus noise). The resulting triplicate data set are then tested for stability (a is −10%, b is +10% and the c point is the raw data). Table 1 shows the result of the stability test for data from the clinical study. Notice that three samples show very high instability in the cancer scores. Samples 138, 207, 34 and 29 all show very high figure of merit. The figure of merit (lower better) should encompass both the degree of score shifting and especially whether or not the score shifts for predicting healthy to cancer or vice versa. These data sets from blind samples are at a high risk of being incorrect in predicted diagnosis.

An incongruent training set model can be used to arbitrate "at risk" patient sample data sets that fail a merit noise test. These points are at risk due to inevitable measurement noise, either random or systematic coupled with extreme topology instability caused by the fact that the blinded sample data point sits on a very steep slope on most if not all of the bi-marker planes so that small perturbations yield large swings in score. Table 1 shows samples with noise injected. Each sample has three values, 1) plus noise, 2) minus noise and 3) raw data no noise. These samples show cancer scores that jump from disease to non-disease and back with the injection of +−10% noise. These sample data in this case are judged to be unstable. The level of instability is not exactly defined and adjustments can be made for various levels of noise injection. In this case, these are corrected with +−10% noise and a stability score of greater than 200 (note that stability score and cancer score are two distinctly different number with different meanings).

Figure 9:
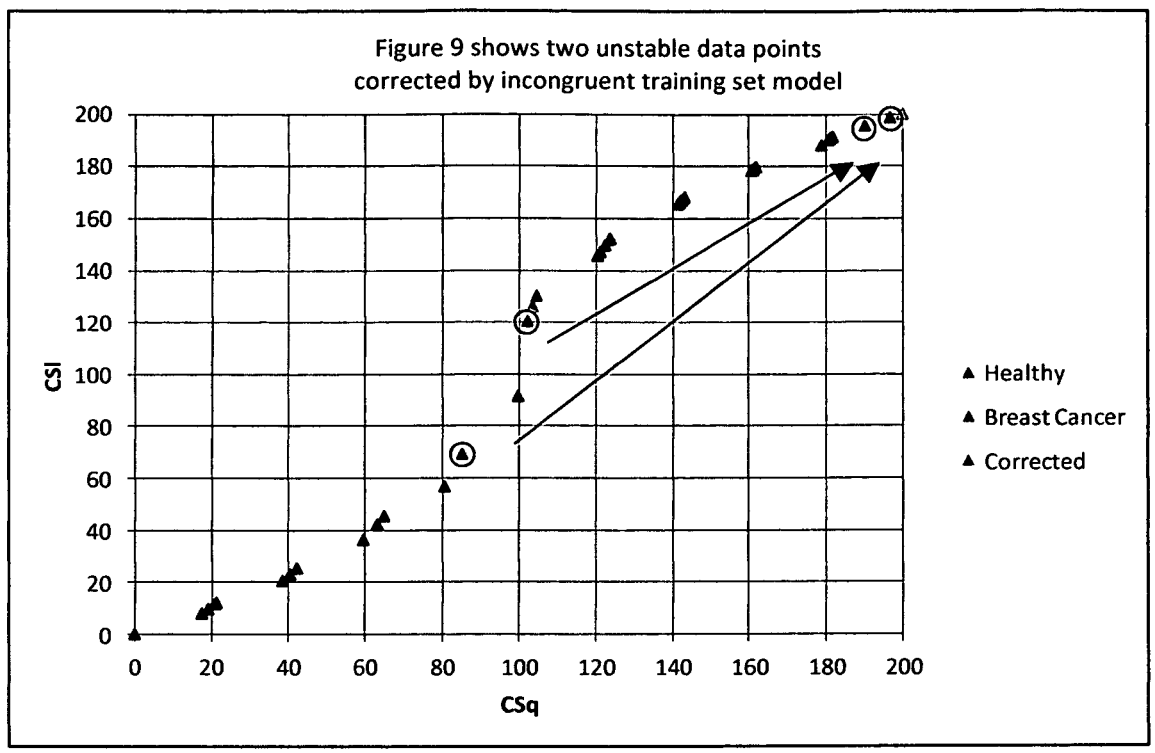
FIG. 9 shows results of the blind tests with two samples that failed the topology instability test and were corrected with the incongruent algorithm.

Measurement noise can be arbitrated with this incongruent second algorithm. The incongruent algorithm used for arbitration can use used to correct these "at risk" patient samples sets even if it has slightly less predictive power than the main algorithm as it will improves the odds that the point is correct. In this case, two were corrected (see FIG. 9); sample 138 had a score of 85 non-disease and was corrected to 195 with the incongruent algorithm (this point was stable with algorithm I, sample 34 had a score of 102 (linear method) and was corrected to 198 again with algorithm II. Samples 29 and 207 were not changed by the incongruent algorithm.

The incongruent training set model (Algorithm II) used 105 bi-marker planes and is incongruent to the primary training set model (Algorithm I) in that these same samples show as stable in the Algorithm II stability test. Testing the incongruent training set model is done in exactly the same way as for the primary training set model. Note that logistic regression method could be used to calculate these sample scores also. Algorithm II has a high predictive power so it was used. An arbitrating training set model can be used even if its predictive power is less (preferably, not less than 50% predictive power though) than the main algorithm as long as it has a likely correct result without instability. Notice that the correction is dramatic for the blinded samples in question that failed the noise test. These samples actually were all cancer with high scores. Eight of the ten bi-marker planes for these samples were on topology with very high unstable grid points. Thus the scores were at risk and indeed were incorrect (one was incorrect and one was uncertain with scores of 100/120. In this case one sample was corrected to improve the predictive power from 97% to 98%, a very significant reduction in error (50%). One sample though uncertain was changed to cancer and also corrected.

Method for Improving Disease State Correlation Binary Outcome
Predictive Power by Excluding an Independent State that Partially
Mimics One of the Outcome States of the Primary Disease Analysis:

Cluster analysis commonly uses three or more independent variables, often a patient's blood serum protein concentrations. The correlation algorithm can act on only a binary outcome of non-disease or disease, but it produces a continuous scoring that more closely relates to a probability of the actual outcome being the two binary conditions. In some cases, there are other conditions, nominally classified as non-disease, that partially mimic the disease state within the population distributions of the biomarkers used. In some of these cases, this non-disease "MIMIC" state can cause a false positive outcome of the correlation analysis. A solution to resolve this kind of false positive result is to create an additional new correlation analysis completely separate from the non-disease or disease analysis. This new correlation analysis preferably uses the exact same biomarker measured data as for the non-disease or disease correlation or it may use some or all different biomarkers. This new correlation analysis provides a result of "non-disease MIMIC" or "disease" or at least produces a score allowing a judgment to be made about the real state of the patient. An uncertain or near transition score for the non-disease or disease analysis coupled with a very low or high score in the non-disease MIMIC or disease correlation can help the physician practitioner improve the disease state judgment and reduce false positive scores.

An example of this situation where a non-disease condition mimics a disease state is the non-malignant condition Benign Prostate Hypertrophy (BPH). This condition will commonly show high levels of at least one biomarker used to diagnose prostate cancer. For example, the biomarker, prostate specific antigen, will be elevated in men with BHP and also with prostate cancer. Table 5 shows that this additional correlation analysis method can discriminate between men with BHP and prostate cancer and, likewise using the same biomarkers but a different training set model, can discriminate between men who are putatively in a non-disease state and those with confirmed prostate cancer in the disease state. In a small fraction of men, a false positive will result with the non-disease versus cancer training set model, but this will be discriminated by the BHP versus cancer training set model. In these cases, two scores, one for putatively non-disease verses cancer and one for BHP verses cancer, will help the physician or other health care practitioner decide the next diagnostic step. For example, for total scoring (for either CS1 or CSq) from 0 to 200 for both models a score of 110 for NOT PROSTATE CANCER OR PROSTATE CANCER indicates a weak score for being cancer positive but also considering the second score of 30 for the BPH or cancer would indicate to the physician practitioner a high likelihood of BPH not cancer. The physician practitioner would use this added information along with other medical information and patient history to decide the next steps in diagnosis.

Several methods for improving the predictive power of traditional proteomics correlation methods for diagnosing disease have been described in this specification. These include: 1) using a meta-variable and pseudo-concentrations values for the correlation, and 2) using special knowledge of topology stability and assay measurement characteristics to adjust bi-marker plane influence in the training set model. Also, methods for finding and correcting blind sample stability problems unique to the particular training set model using an incongruent training set model are described. Additionally, methods for finding and correcting non-disease conditions that partially mimic the training set model for a given disease state are described. All of these methods are complimentary and can be used in concert. For example, adjusting the training set model for areas of high likelihood of instability cannot completely remove this problem from blind sample predictive calculations and thus both methods can be used for improvements in predictive power. The inventors have found that combining these methods can yield predictive powers above 95%, and the breast cancer study discussed in Example 1 yielded over 98% predictive power (100% sensitivity, 97.5% specificity).

Example 1

Clinical Study—Assessment of Breast Cancer Blood Test

The performance of the OTraces BC Sera Dx test kit and OTraces CDx Immunochemistry Instrument System (www.otraces.com) was evaluated in an experiment to assess the risk of the presence of breast cancer. The test kit measures the concentrations of five very low-level cytokines and tissue markers, and uses a training set model that was developed as described above to calculate scores, CSI and CSq, for assessing the risk of breast cancer. The proteins measured were IL-6, IL-8, VEGF, TNFα and PSA. The experiment consisted of measuring about 300 patient samples split roughly 50% between breast cancer cases diagnosed by biopsy and 50% from patients putatively considered non-diseased (or in this case not having breast cancer). Of this group, the biopsy results for 200 samples divided exactly into 50% non-disease and 50% having breast cancer disease and each group was further subdivided into specified age groupings.

The sample analysis results were used to develop a training set model that is predictive of the disease state. The remaining samples (about 110) were then processed as blinded samples through the training set model to obtain resultant cancer risk numerical scores and these scores were disclosed to the host clinical center. These blind sample scores subsequently were analyzed by the clinical center to assess the clinical accuracy of the results.

Two diagnostic models were developed for this experiment, and are referred in this specification as Algorithm I (or Training Set Model I) and Algorithm II (or Training Set Model II), as discussed above. The neighborhood cluster method of analysis was used for both algorithms. The age of the subjects was not used as an independent variable but rather as a meta-variable to transform the measured concentrations into new independent variables, referred to in this specification as pseudo-concentrations, which were used directly in the correlation analysis. The difference between Algorithm I and Algorithm II is the number of new independent variables used in the correlation. Algorithm I uses five pseudo-concentration variables in a ten dimensional cluster space. This space can be viewed by the human eye via projection or cuts through this multidimensional space to look at a two-dimensional bi-marker plane. There are ten such planes in Algorithm I.

Algorithm II uses ten-fold more created independent variables, such that there are about 100 bi-marker planes. It is expected that 200 samples are sufficient for the training set model such that it reasonably closely models the general population. Secondary or the incongruent training set model was developed from the same 200 sample training data set. The training set model is the primary scoring method used to describe the results in this specification. The incongruent training set model is used to arbitrate primary training set model calculated cancer scores that are considered unstable; that is, scores that rest on an area of topological instability. Though the incongruent training set model is somewhat less accurate on blind samples, although it still can arbitrate the primary training set model and thus improve predictive power.

The foregoing clustering method of analysis has the significant advantage, relative to logistic regression, of being able to accommodate highly non-linear trends in the independent variables used to create the calculation outcome. The outcome is either disease or non-disease (in this case cancer or not cancer) and it is based upon the pseudo-concentrations to the training set model calculations. The disadvantage of this method is the highly non-linear areas can be associated with very steep topology slopes. Thus, an unknown (or blind) sample may be sitting on a steep peak or deep sharp valley which amplifies has the effect of amplifying small errors in the computed pseudo-concentrations. We assessed the stability of the calculated scored with a proprietary stability test and then used Algorithm II to arbitrate algorithm I if Algorithm II for samples that showed stability.

Figure 10:
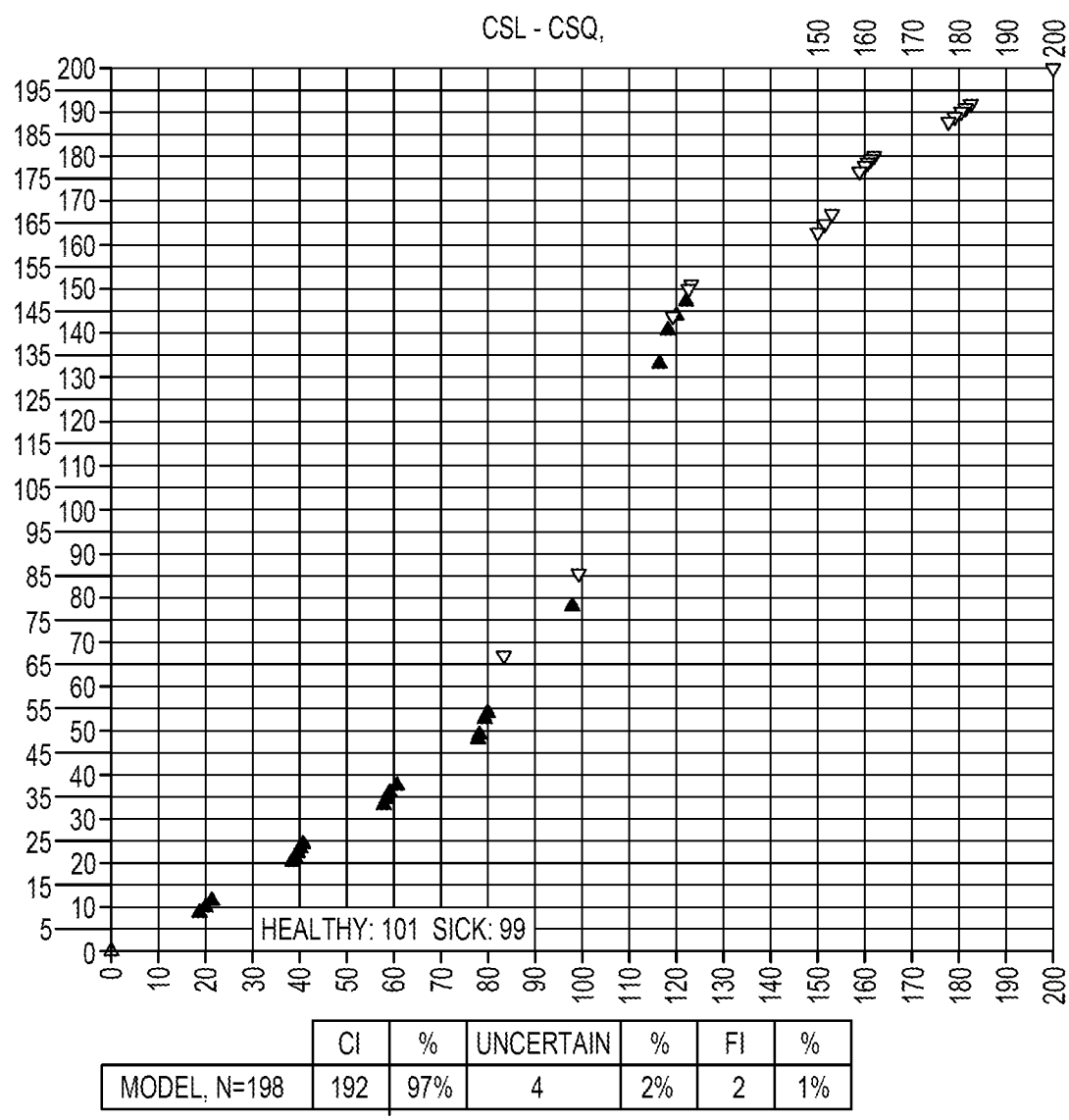
FIG. 10 shows the results of the clinical study for breast cancer in this case the training set cancer scores are shown for Training Set Model I using 10 bi-marker planes.
Figure 11:
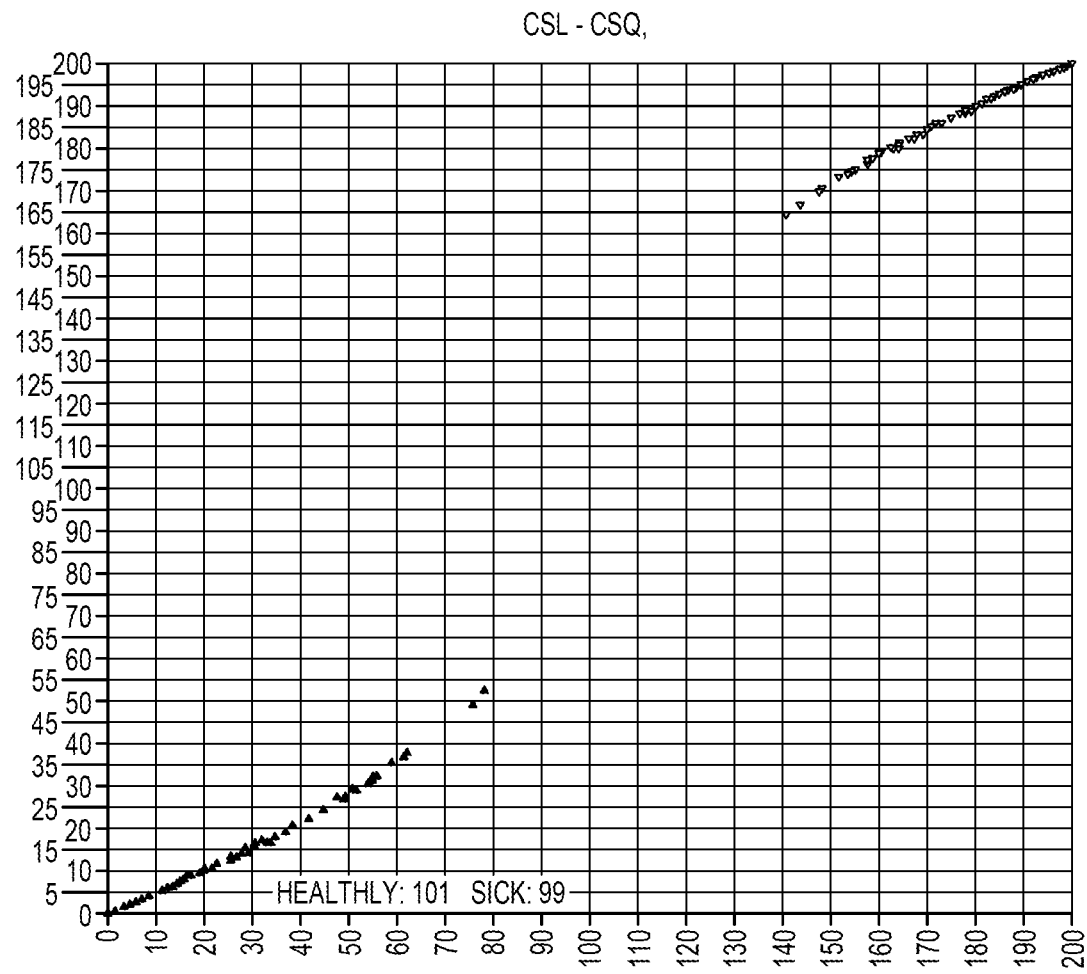
FIG. 11 shows the results of the clinical study for breast cancer in this case the training set cancer scores are shown for Training Set Model II using 105 bi-marker planes.
Figure 12:
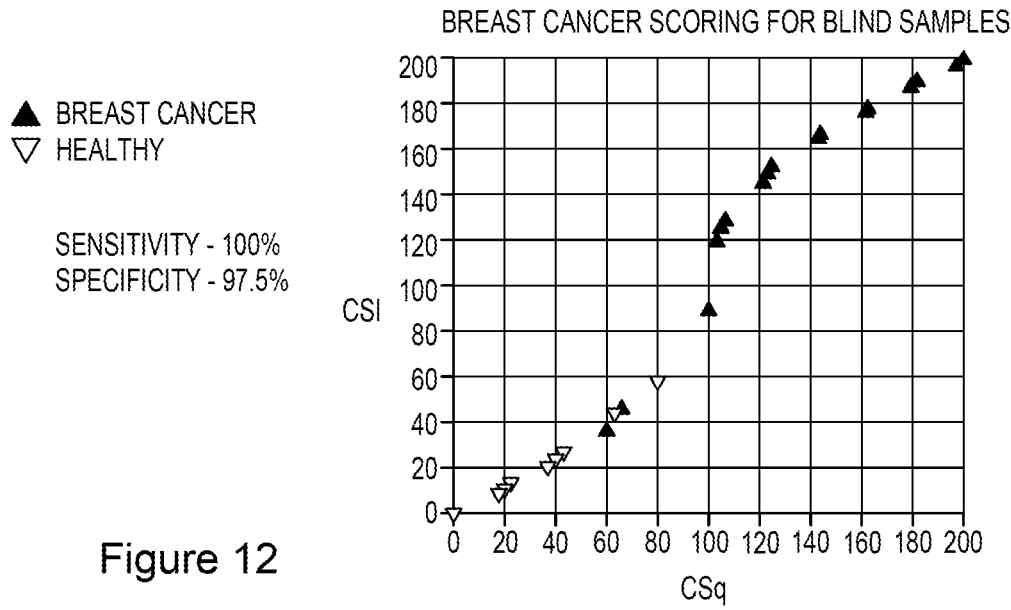
FIG. 12 shows the results with actual diagnosis for the blind samples run the clinical study.

FIGS. 10, 11 and 12 show the Algorithm I training set results. The model itself consists of 10 bi-marker planes of 40,000 topology points each scored for non-disease and disease (here, breast cancer) by the clustering method. The ability of the model to separate the two sets of non-cancer and cancer is shown in these figures. The model must be constructed from very close to or preferably exactly 50% by 50% or very close to of the two outcome states. Also, the method uses age as transforming meta-variable. The training set samples had samples distributed across all age groups of interest. Model (FIG. 10) for Algorithm 1 was constructed from 100 healthy women and 98 breast cancer women.

The summary table on FIG. 10 shows the numerical results, where N=198 is the number of samples. CI is correctly called samples and FI is falsely called samples, and 4 samples were deemed uncertain.

A secondary training set model was developed to discriminate the four uncertain samples that resulted from the use of the primary training set model. This model is the incongruent training set model. This secondary model uses the same training set data as the primary FIG. 11 shows the results for the incongruent training set model calculations. Algorithm II shows 100% separation with over 60 points of separation.

Results of Testing Blind Samples in the Breast Cancer Study:

FIG. 12 shows the results for the blind samples evaluated in the clinical study. The results show 100% sensitivity and 97.5% specificity. The oncologists at the clinical study center set the diagnostic transition value such that the breast cancer positive samples were all identified correctly. Thus, two non-disease samples were called positive for cancer. This is medically sound as the samples judged positive will all get the next diagnostic step, imaging mammography. Many women do not get imaging mammography because they do not live near enough to facilities with the medical equipment. However, their blood can be drawn remotely from the clinical lab and shipped on ice to a lab in a major city.

Example 2

Use of Meta-Variable "Age" to Improve Diagnostic Accuracy

Table 2 shows the tabulated results for an 868 subject sample clinical study for breast cancer. Table 3 shows the comparison of various methods for the correlation calculation. The standard method, logistic regression, showed only an 82% predictive power. Standard Neighborhood Cluster analysis improved on this, yielding about an 88% predictive power. The methods described in this specification using the meta-variable and weighting approaches, topology stability conditioning, immune system response grouping and weighting conditioning for assay performance—coupled with instability testing of blind samples and incongruent algorithm correction—yielded greater than 97% predictive power.

Example 3

Use of Meta-Variable "Age" to Improve Diagnostic Accuracy in an Ovarian Cancer Study Table 4 shows the results of a study of 107 women with ovarian cancer or not having ovarian cancer using the meta-variable method described herein. This study did not use all of the predictive power improvements described in this specification but still achieved a relatively superior predictive power of about 95%.

Example 4

Use of Meta-Variable "Age" to Improve Diagnostic Accuracy in Prostate Cancer Table 5 shows the results of a study of 259 men either having prostate cancer or benign prostate hyperplasia (BPH) using the meta-variable method described in this specification. This study also did not use all of the predictive power improvements described herein but still achieved a relatively superior predictive power of about 94%. Note that BPH is by far the most common condition that causes false positive results in the current PSA test for prostate cancer. Men with BPH are about 4 out of five positives in conventional diagnoses of prostate cancer resulting in most prostate cancer biopsies being negative. The meta-variable method is able to correct these incorrect diagnoses as discussed above.

The foregoing results in Examples 3 and 4 (for ovarian cancer and prostate cancer, respectively, did not use the meta-variable or influence adjustment methods (LOD, sub-populations groupings and instability) nor the blind sample stability method as these were not discovered by the inventors when this data was measured.

II. Diagnostic Methods Using Preferred Analyte Categories and Analytes Measured Below Conventional Limits of Detection.

The present invention is also based on a discovery that certain immune system proteins permit a diagnosis of the risk of a given disease at measured concentrations substantially below those presently utilized for commercial diagnostic testing. These include: cytokines, whose functionality, primarily but not totally as signaling proteins, are in certain groups; immune system inflammatory markers, tumor anti-angiogenesis, cell apoptosis and tumor vascularization markers as well as known tumor tissue markers.

The inventors have shown that selecting a few very low abundance proteins LAPs and using non-traditional methods for correlation analysis and for determining concentration from immunoassay analysis methods greatly improves predictive power. These low level proteins termed signaling proteins (that is, proteins that serve one or more of several types of function in signaling networks) are either acting from direct immune system response to the presence of the tumor or are actions by the tumor directing the organism to provide needed physiological responses that the tumor needs to progress. Furthermore selecting a few LAPs (preferably, about 6 or less) solves intractable over sampling and training set sizing problems. The fact that these proteins are at or lower than the traditionally defined detection limits previously has hindered research into their usefulness.

The present invention also is based upon a surprising discovery that concentration values below the level of detection, as determined conventionally, provide meaningful information in a correlative risk assessment for disease. Such information has traditionally not used in clinical diagnosis because of their inaccuracy. However, the inventors have found that it is effective to provide a straight-line curve fit from the LOD calibration point to the lowest signal value in a test run and to utilize those values. Doing so provides a smooth Gaussian distribution for the population distribution analysis and also, surprisingly, accurate cancer score predictions. In this diagnostic method, no reading below the LOD should be reported that is lower that what is normally seen in large-scale population assessments of this marker. For example, if the signal level (or measured concentration) is below the LOD, use of the technique described herein is appropriate down to the lowest level found in normal serum.

Thus, where the LOD for IL-6 is about 250 fg/ml but reported values are found in serum as low as 10 fg/ml, that level should be the lowest used in the assays according to the present invention. Also, no value can be zero or negative. This approach works with a variety of conventional standard curve creation strategies.

The inventors have surprisingly found that using immune system proteins, cytokines, whose functionality are in certain groups; immune system inflammatory, tumor anti-genesis, cell apoptosis and tumor vascularization markers as well as known tumor tissue markers predictive power can be achieved such that false negative performance of the correlation model better than 95% with false positive performance also better than 95%. These proteins require methods for extracting useful concentration information at levels well below 1 pg/ml for some markers. For a particular proteomic test panel for breast cancer for example that uses PSA for the tissue marker, IL-6 for inflammatory response, IL-8 for inflammatory and vascularization, VEGF for vascularization and TNFα for anti-tumor genesis, predictive powers have been produced above 98%. Several of these markers have significant population distributions below 1 pg/ml (down to less than 50 fg/ml). This has discouraged researchers from exploring the use of these proteins for clinical diagnostics methods.

It is contemplated that the present invention includes diagnostic tests in which, for example, breast cancer is predicted using immune system inflammatory (IL-6, IL-8), vascularization (IL-8, VEGF), Anti-tumor genesis (TNFa) proteins and the tissue marker (PSA). Other markers may be used that fall within these categories, such as CA 19.9 for PSA, tissue markers; or IL-1 added or substituted for IL-6. For prostate cancer, it is contemplated that a predictive assay be utilized that includes immune system inflammatory markers (IL-6, IL-18), vascularization markers (IL-8, VEGF), anti-tumor genesis (TNFa) proteins and a tissue marker (PSA). Other markers may be used that fall within these categories (for example, IL-1 added or substituted for IL-6). Contemplated ovarian cancer status predictions are made using immune system inflammatory markers (IL-6, IL-18), vascularization (IL-8, VEGF), anti-tumor genesis (IL-12) proteins and the tissue marker (CA 125). Other markers may be used that fall within these categories (for example, TNFa for IL-12).

Also the inventors have found that correlation analysis requires 100% of the population have viably accurate measurements or the predictive power is compromised. Viably accurate does not mean that the accuracy of these measurements must be equivalent to expectations of measurements from clinical diagnostics used today in the clinical lab. In the clinical lab, when a number for concentration is needed for diagnosis the point on the assay calibration curve must be above the analytical sensitivity which means 99.7% certainty of the result being within 3 standard deviations of the actual value.

Any samples having indeterminate or 0 values for a marker un-anchors the correlation calculation rendering this sample wholly incorrect. The combination of a few LAP signaling proteins and very low-level concentration measurement extraction method yields significant improvement in results. At very low levels below the conventional assay limit of detection acceptable, accuracy is obtained by simply using a straight line from the LOD to the lowest signal sample and using the lowest physiological level found in serum as the concentration for this point in the test run of many samples. Sample points between the LOD and the lowest reading are estimated on this straight line. Other standard curve fit methods may also be used. These improvements are significant enough that the measurement panel may be useful for screening for cancer (yielding a 98% or greater predictive power).

The present inventors have found that using immune system proteins, cytokines, whose functionality are in certain groups; immune system inflammatory, tumor anti-genesis, cell apoptosis and tumor vascularization markers as well as known tumor tissue markers predictive power can be achieved such that false negative performance of the correlation model better than 95% with false positive performance also better than 95%. These proteins require methods for extracting useful concentration information at levels well below 1 pg/ml for some markers.

For a particular proteomic test panel for breast cancer, for example, that uses PSA for the tissue marker, IL-6 for inflammatory response, IL-8 for inflammatory and vascularization, VEGF for vascularization and TNFα for anti-tumor genesis predictive powers have been produced above 95%. All of these markers have significant population distributions below 1 pg/ml (down to less than 100 fg/ml). The correlation analysis requires a very high percentage (100%) of the population have viably accurate measurements or the correlation fails. Any samples having indeterminate or 0 values for a marker un-anchors the correlation calculation possibly rendering this sample wholly incorrect. The combination of a few LAP signaling proteins and very low level concentration measurement extraction method yields significant improvement in results. Significant enough the measurement panel may be useful for screening for cancer.

Figure 13:
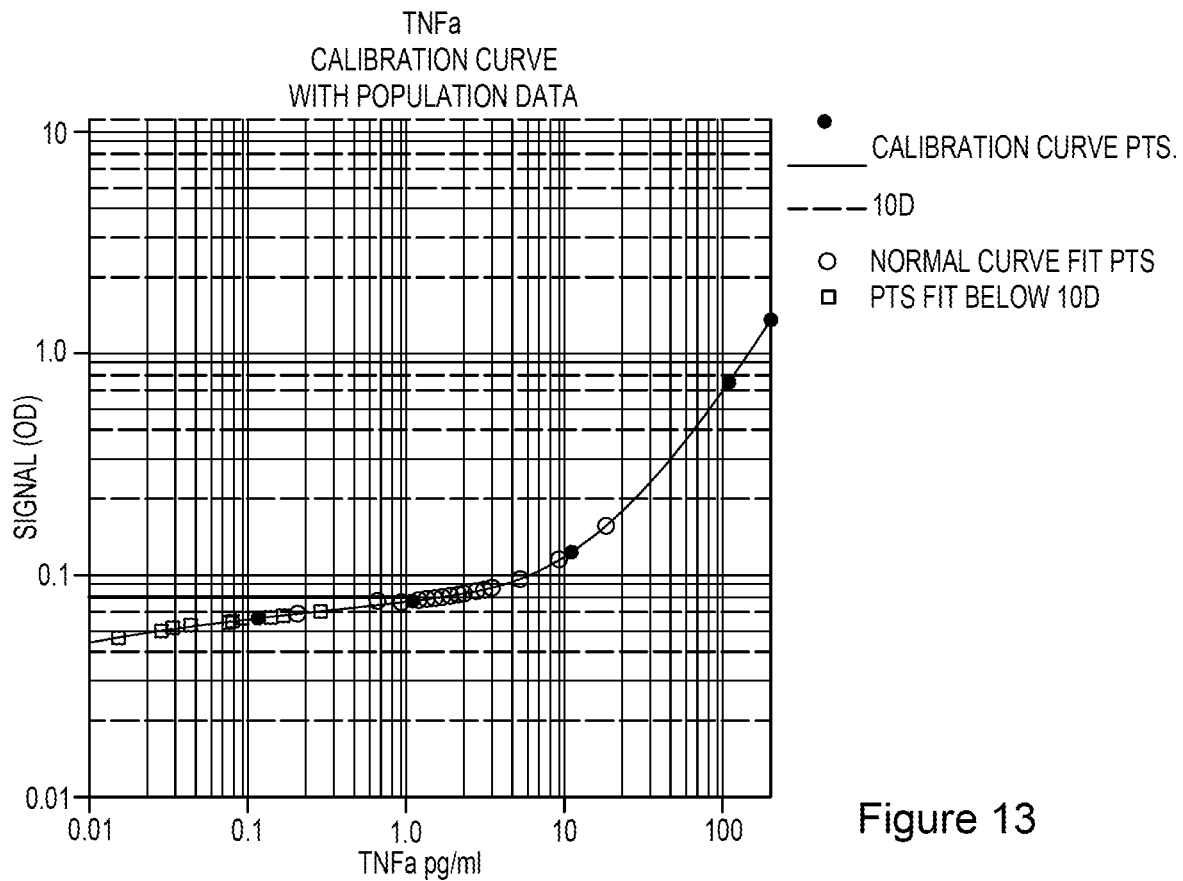
FIG. 13 shows a calibration curve for the protein TNFa with blind sample data points.

FIG. 13 shows a typical ELISA calibration curve for TNFa. In this case, the Limit of Detection (LOD) is about 1.0 pg/ml, which about the best that can achieved with current rapid screening measurement technologies. Notice that a significant percentage of the population is below the LOD. Surprisingly, these data points are very useful and in fact necessary for a high predictive power correlation to be achieved.

In the clinical laboratory it is common practice that the limit of detection is defined as two standard deviations above a zero calibrator where the standard deviation is calculated typically using twenty zero standards. Results measured that are below this level are typically not reported or, if reported, are flagged as below the LOD. When a single-analyte assay is used for clinical diagnostic purposes, it must have an accurate stand-alone number above the LOD to properly offer diagnostic information to the physician practitioner and the conventional method is required.

Figure 14:
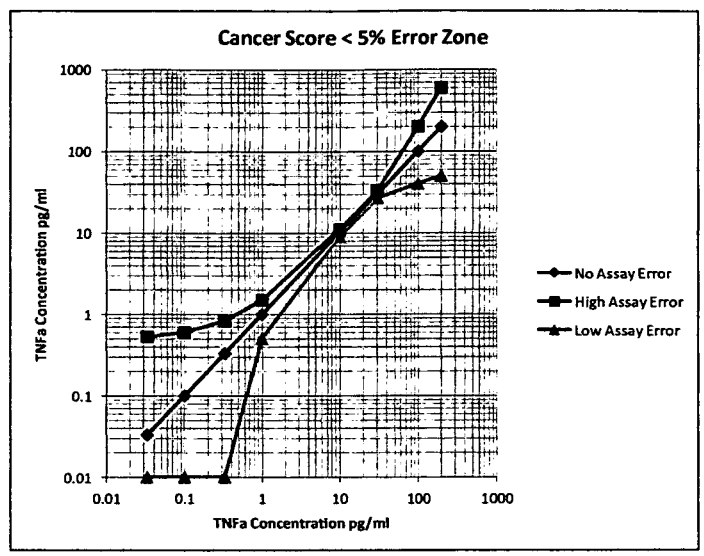
FIG. 14 shows the TNFa protein assay error bars for 5% cancer score error.

In the case of diagnostic assays using low level signaling proteins, as described in this specification, measurements for the purpose of reliably scoring the probability of non-disease vs. disease states do use these lower-than-LOD measurements. FIG. 14 shows the data from FIG. 13 but with error bars showing the amount of error allowable to keep the calculated cancer score error less than 5%. At the extreme low levels of detection at or below the LOD a relatively amount of error is tolerated. The same is true at very high concentrations.

The critical area for the calibration curve of a diagnostic assay is where the diagnosis prediction score is in the range of scores that clearly indicate a state of non-disease to the scores that clearly indicate a state of disease. Also, note that if the data below the LOD is either eliminated or reported as 0 the scoring for that patient can simply go to extreme errors, low score healthy can go to high score cancer. This is because the algorithm must be able to "anchor," all five markers to some general level at the extremes and be accurate at the transitions. If one marker is un-anchored the calculated results is based solely upon only the other 4. There could well be conditions where elevated results for the 4 are not indicative of cancer and all five are needed and must be elevated to indict cancer and to accurately make the score. Each individual marker has a limited effect on the individual cancer score and this effect is weighted by the markers real influence and its probable level of noise based upon its position of the calibration curve.

For example, the breast cancer test panel discussed herein, which includes PSA in the panel, shows only a 3 to 4% improvement in overall training set model predictive power for an overall analysis of a large training set (200 samples). However, removing it from one blind sample can drive the scoring from the training set model to be off enough that this sample can shift from healthy or cancer (for example, 50 score to 180 on the 0 to 200 scale). These blind samples may be rare but only one out of 100 yields a drop in predictive power of 1%. With these methods the inventors have achieved 98% predictive power, thus 1% loss is very significant. A blind sample data point for PSA, by way of example, if estimated at very low levels of around 10 fg/ml can be off by 20 fold without producing a significant cancer score error. On the other hand if PSA is omitted or called zero the cancer score becomes "unanchored" by the low PSA level and if not included can have a shift in cancer score to render it completely incorrect.

Understanding the uncertainties involved at these low measurement levels is important. For measurement samples run in duplicate, the confidence level at 1.5 standard deviations from the nominal measurement point is 95%. At 0.75 standard deviations from the nominal measurement point the confidence is 67%. This level of accuracy is more than adequate at very low levels in these methods and having no number at all can render the method not useful.

The method, according to the present invention, for assessing the value of the measured points for correlation assessments is governed by the following:

1) The traditional calibration curve should extend from the LOD for the assay as assessed during development to as high as possible using typical immunoassay methods, for example, ELISA, through the population dynamic range.
2) Below the LOD, all points are assumed to have significant noise and thus actual measurement points may be below the lowest calibrator. In these cases, the reported results must be:
    a. Above zero, negative concentrations are not possible and zero values in the correlation algorithm are just as deleterious as no value to the accuracy of results.
    b. Determined rather than simply having a value assigned to all undetermined patient sample point concentrations, which would distort the population distributions needed for the subgroup training set model construction
    c. Reported no lower that is normally seen in large-scale population assessments of this marker.

The inventors surprisingly have found that simply using a straight line curve fit from the LOD calibration point to the lowest signal value in the test run is adequate. This provides a smooth Gaussian distribution for the population distribution analysis and accurate cancer score calculations. Using this approach, any number of different standard curve creation strategies will work if the above rules are followed.

It is contemplated that the technique disclosed for utilizing analyte concentrations below the convention LOD may be used for any assay that utilizes measured concentrations of markers, for example, in patient samples. Preferred embodiments include diagnostic assays for various diseases such as solid tumors including cancers of the prostate, lung, breast and ovary. These techniques may optionally but preferably be combined with the other data analysis and diagnostic techniques described elsewhere in this specification.

Also, a person skilled in the art will understand that the analysis errors caused by the correlation method utilized, such as bi-marker plane topology instabilities, or from inadequate training set size as are described elsewhere in this specification is caused by completely different phenomena and requires a completely different method for mitigation. For example, certain disclosed error and correction methods are appropriate for extreme non-linear (or very steep) slopes upon which the test sample point sits on the correlation bi-marker topology. And such errors can be found by injection of artificial noise and arbitration with an incongruent training set model. The noise referred to here is inherent in the assay measurement that results from experimental error, but it is critical that the effect of this noise on the resultant cancer score be understood.

III. Implementation Through Computer Systems

Implementations of the various techniques described herein may be implemented in digital electronic circuitry, or in computer hardware, firmware, software, or in combinations of them. Implementations may implemented as a computer program product, for example, a computer program tangibly embodied in an information carrier, for example, in a machine-readable storage device or in a propagated signal, for execution by, or to control the operation of, data processing apparatus, for example, a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, for example, magnetic, magneto-optical disks, or optical disks. Information carriers suitable for embodying computer program instructions and data include all forms of non-volatile memory, including by way of example semiconductor memory devices, for example, EPROM, EEPROM, and flash memory devices; magnetic disks, for example, internal hard disks or removable disks; magneto-optical disks; and CD-ROM and DVD-ROM disks. The processor and the memory may be supplemented by, or incorporated in special purpose logic circuitry.

To provide for interaction with a user, implementations may be implemented on a computer having a display device, for example, a cathode ray tube (CRT) or liquid crystal display (LCD) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

Implementations may be implemented in a computing system that includes a back-end component, for example, as a data server, or that includes a middleware component, for example, an application server, or that includes a front-end component, for example, a client computer having a graphical user interface or a Web browser through which a user can interact with an implementation, or any combination of such back-end, middleware, or front-end components. Components may be interconnected by any form or medium of digital data communication, for example, a communication network. Examples of communication networks include a local area network (LAN) and a wide area network (WAN), for example, the Internet.

The invention described in this specification generally relates to methods of improving diagnostic accuracy or predictive power of proteomic and metabolomic correlation methods for predicting disease states. While certain exemplary embodiments have been described above in detail and shown in the accompanying drawing figures, it is to be understood that such embodiments are merely illustrative of and not restrictive of the broad invention. In particular, it should be recognized that the teachings of the invention apply to a wide variety of diseases. Also, while the preferred embodiments of the present invention relate to the diagnosis of human diseases in a subject (or patient) for whom a disease diagnosis is desired, it is expressly contemplated that the methods and systems disclosed in this specification are useful for diagnostic purposes in non-human species, particularly primates and other mammals, and as such are part of the present invention.

While certain features of the described implementations have been illustrated as described herein, many modifications, substitutions, changes and equivalents will now occur to those skilled in the art. Thus, it will be understood that the invention is not limited to the particular embodiments or arrangements disclosed, but is rather intended to cover any changes, adaptations or modifications which are within the scope and spirit of the invention as defined by the appended claims.

REFERENCES

All of the journal articles and all other publications, patents and texts mentioned in this specification are incorporated by reference in their entireties, including the following.

(1) Drukier, et al., "High-Sensitivity Blood-Based Detection of Breast Cancer by Multi Photon Detection Diagnostic Proteomics," Journal of Proteome Research 2006, 5:1908, 1915.

(2) Lokshin et al., "Multimarker assay for early diagnosis of ovarian cancer," American Association for Cancer Research, Amer Assoc Cancer Res 2006, 47:653. CME: Disclosure.

(3) Drukier, et al., Ultra-Sensitive Immunoassays Using Multi Photon Detection in Diagnostic Proteomics of Blood," Journal of Proteome Research 2005, 4:2375-2378.

(4) Drukier, "Supersensitive Immunoassays," U.S. Pat. No. 7,604,956 (2009).

The invention claimed is:

1. A method for diagnosing cancer, comprising the steps of:
   a) receiving concentrations of at least five predetermined analytes in a blind sample from a subject, wherein at least one of the predetermined analytes is a low abundance protein;
   b) selecting one or more meta-variable associated with the subject, which varies in a population associated with the subject for members of the population who are known either to have or not have the disease, wherein the disease is breast cancer or ovarian cancer;
   c) transforming the concentrations of the analytes as a function of one or more population distribution characteristics and the one or more meta-variables to compute a pseudo-concentration that represents each analyte, wherein the pseudo-concentration is computed as a unitless, clinically predictive measure of each analyte;
   d) scoring the pseudo-concentrations against a training set model of pseudo-concentrations determined for members of the population who are known either to have or not have the disease, wherein the training set model utilizes a multidimensional analysis comprising at least five orthogonal axes, wherein the score is determined by plotting each pseudo-concentration in a bi-marker plane with data points of the training set model and determining the distance from each pseudo-concentration to the nearest measured data points of the training set model;
   e) diagnosing the disease by determining whether the score of the pseudo-concentrations indicates that the subject has the disease, wherein false negative and false positive performance of the training set model is at least better than 90%; and
   f) administering one or more anti-cancer drugs capable of treating the indicated disease.

2. A method for preparing a training set model capable of diagnosing a disease, comprising the steps of:
   a) determining concentrations of at least five predetermined analytes in a training set of samples from a group of subjects, wherein at least one of the predetermined analytes is a low abundance protein;
   b) selecting a meta-variable associated with the subjects, which varies in a population associated with the subjects for members of the population who are known either to have or not have the disease, wherein the disease is breast cancer or ovarian cancer;
   c) transforming the concentrations of the analytes as a function of one or more population distribution characteristics and the meta-variable to compute a pseudo-concentration that represents each analyte, wherein the pseudo-concentration is computed as a unitless, clinically predictive measure of each analyte;
   d) preparing the training set model from the pseudo-concentrations determined for members of the populations who are known either to have or not have the disease, wherein the training set model diagnoses the disease by scoring the pseudo-concentrations against the training set model by plotting each pseudo-concentration in a bi-marker plane with data points of the training set model and determining the distance from each pseudo-concentration to the nearest measured data points of the training set model, wherein the training set model utilizes a multidimensional analysis comprising at least five orthogonal axes, wherein false negative and false positive performance of the training set model is at least better than 90%;
   e) diagnosing the disease on the basis of the training set model; and
   f) administering one or more anti-cancer drugs capable of treating the indicated disease.

3. The method of claim 2, wherein the at least five predetermined analytes are selected from the group consisting of at least four, at least five and at least six analytes.

4. The method of claim 2, wherein the meta-variable is age.

5. The method of claim 2 further comprising a comparing step, wherein the comparing step includes a correlation step selected from a group consisting of clustering, neighborhood search, regression or wavelet analysis.

6. The method of claim 2 further comprising a comparing step, wherein the comparing step further comprises using an incongruent training model.

7. The method of claim 2, wherein the model is computer implemented and further comprises outputting a score.

8. The method of claim 1, wherein the steps of transforming, comparing and determining are repeated with a second training set model that identifies non-disease conditions in the subject's population that partially mimic the serum analyte changes but are not the disease state.

9. The method of claim 8, wherein the determining step provides a risk assessment for three states: non-disease, non-disease condition that partially mimic the disease state, and the disease state.

10. The method of claim 2, further comprising normalizing the training set model and smoothing irregularities or noncontiguous distributions of the concentrations using a logarithm of the ratios of the measured concentrations and the age adjusted mean values of the concentrations of proteins for the non-disease and disease states for which the individual sample is predictive and the ratio of the concentrations of the proteins for the non-disease and disease states, such that a distribution of a resultant new independent variable to be used in the correlation is compressed to aid a correlation calculation.

11. The method of claim 2, wherein the meta-variable is selected from the groups consisting of: pre, peri and post menopausal status, pubescence, body mass, geographic location of the source of the sample, body fat percent, age, race or racial mix or ethnicity, species or era of time.

12. The method of claim 2, wherein the relationship between independent variables and the meta-variable encompasses population distribution characteristics of the independent variables selected from the group consisting of: the degree of nonlinearity of the relationship between the states of disease and non-disease, one or more groups, group mean values, group average values, group median values and group dynamic range values.

13. The method of claim 2, further comprising a correcting step for the training model that includes adjusting a weighting influence of individual analytes based upon knowledge of the individual biomarkers' up or down regulation characteristics in the course of disease progression in a typical subject in the relevant population.

14. The method of claim 2, further comprising a correcting step for the training set model that includes adjusting a weighting influence of individual biomarkers based upon the bi-marker plane topology instabilities.

15. The method of claim 2, further comprising a correcting step for the training set model that includes adjusting a weighting influence of individual biomarkers based upon the bio-marker assay uncertainties.

16. The method of claim 2, further comprising a correcting step for the training set model by that includes using an incongruent training set model to correct individual blind samples that show instabilities in outcome prediction due to topology instabilities.

17. The method of claim 2, wherein baseline values of individual protein concentrations are determined for a subject over time including a period of time when the subject is in the non-disease state rather than the population value.

18. The method according to claim 13, wherein the measured analytes are low abundance signaling proteins that include at least one analyte in each of at least three of the categories selected from the groups consisting of: immune system inflammatory, angiogenesis, cell apoptosis, vascularization proteins and tissue markers.

19. The method as provided in claim 18, wherein one or more of the biomarkers are very low abundance proteins with concentration levels below about 1 pg/ml in samples drawn from at least about 20 percent of the relevant population for a given subject.

20. The method of claim 2, wherein the concentration values for at least one of the determined analytes are below the LOD, wherein the concentration value for such analyte(s) is determined by a curve fitting method between the LOD and the lowest reading for the analyte, and wherein no analyte is given a zero or negative value, and no analyte is given a value less than a lowest accepted value for that analyte in similar samples the population.

* * * * *